US007000458B2

(12) United States Patent
Sogo et al.

(10) Patent No.: US 7,000,458 B2
(45) Date of Patent: Feb. 21, 2006

(54) WEIGHING EQUIPMENT FOR CONCRETE MATERIAL

(75) Inventors: Shigeyuki Sogo, Kiyose (JP); Ryuichi Chikamatsu, Kiyose (JP); Koji Watanabe, Kiyose (JP)

(73) Assignee: Obayashi Corporation, Osaka (JP)

( * ) Notice: Subject to any disclaimer, the term of this patent is extended or adjusted under 35 U.S.C. 154(b) by 210 days.

(21) Appl. No.: 10/481,454

(22) PCT Filed: Jun. 10, 2002

(86) PCT No.: PCT/JP02/05721

§ 371 (c)(1),
(2), (4) Date: Dec. 19, 2003

(87) PCT Pub. No.: WO03/000478

PCT Pub. Date: Jan. 3, 2003

(65) Prior Publication Data

US 2005/0073904 A1    Apr. 7, 2005

(30) Foreign Application Priority Data

Jun. 20, 2001   (JP)   ............................. 2001-185885
Jun. 20, 2001   (JP)   ............................. 2001-185981

(51) Int. Cl.
*G01N 19/10* (2006.01)

(52) U.S. Cl. ......................................................... 73/73

(58) Field of Classification Search ..................... None
See application file for complete search history.

(56) References Cited

U.S. PATENT DOCUMENTS

2002/0093875 A1 *   7/2002   Rondeau et al. ............... 366/8

FOREIGN PATENT DOCUMENTS

JP   2-170037   6/1990

(Continued)

OTHER PUBLICATIONS

Cement & Concrete 2001 3, No. 649, Japan Cement Association, pp. 54-58.
Shigeyuki Sogo et al. entitled *"DEVELOPMENT OF A HIGH RELIABILITY CONCRETE PRODUCTION SYSTEM (PART 1)"*, Proposal for New Batching Method by Immersing Sand in Water to Facilitate Accurate Measurement, pp. 57-64, Jul. 10, 2000.

(Continued)

*Primary Examiner*—Hezron Williams
*Assistant Examiner*—Paul M. West
(74) *Attorney, Agent, or Firm*—Wenderoth, Lind & Ponack, L.L.P.

(57) ABSTRACT

A measuring apparatus (1) for concrete materials, comprising an aggregate hopper (3) as aggregate feed means for feeding fine aggregate (2) as aggregate, a water supply pipe (4) as water supply means, an aggregate measuring bin (51) for storing and measuring the fine aggregate (2) supplied from the aggregate hopper (3), a measuring tank (5) for storing the fine aggregate (2) supplied from the aggregate hopper (3) as water-immersed aggregate together with water supplied through the water supply pipe (4), a load cell (6) as water-immersed aggregate mass measuring means for measuring the mass of the water-immersed aggregate in the measuring tank, an electrode sensor (7) as water level measuring means for measuring the water level of the water-immersed aggregate in the measuring tank (5), and a water level holding device (8) as water level holding means for holding the water level of the water-immersed aggregate in the measuring tank (5) at a desired water level.

9 Claims, 4 Drawing Sheets

FOREIGN PATENT DOCUMENTS

| | | |
|---|---|---|
| JP | 8-304257 | 11/1996 |
| JP | 2000-61926 | 2/2000 |
| JP | 2000-84921 | 3/2000 |
| JP | 2000-84922 | 3/2000 |
| JP | 2002-154113 | 5/2002 |

OTHER PUBLICATIONS

Study on High Reliability Concrete Production System with New Batching Method by Immersing Sand in Water, No. 676. V-51, 19-26, 5/2001, Japan Society of Engineers.

* cited by examiner

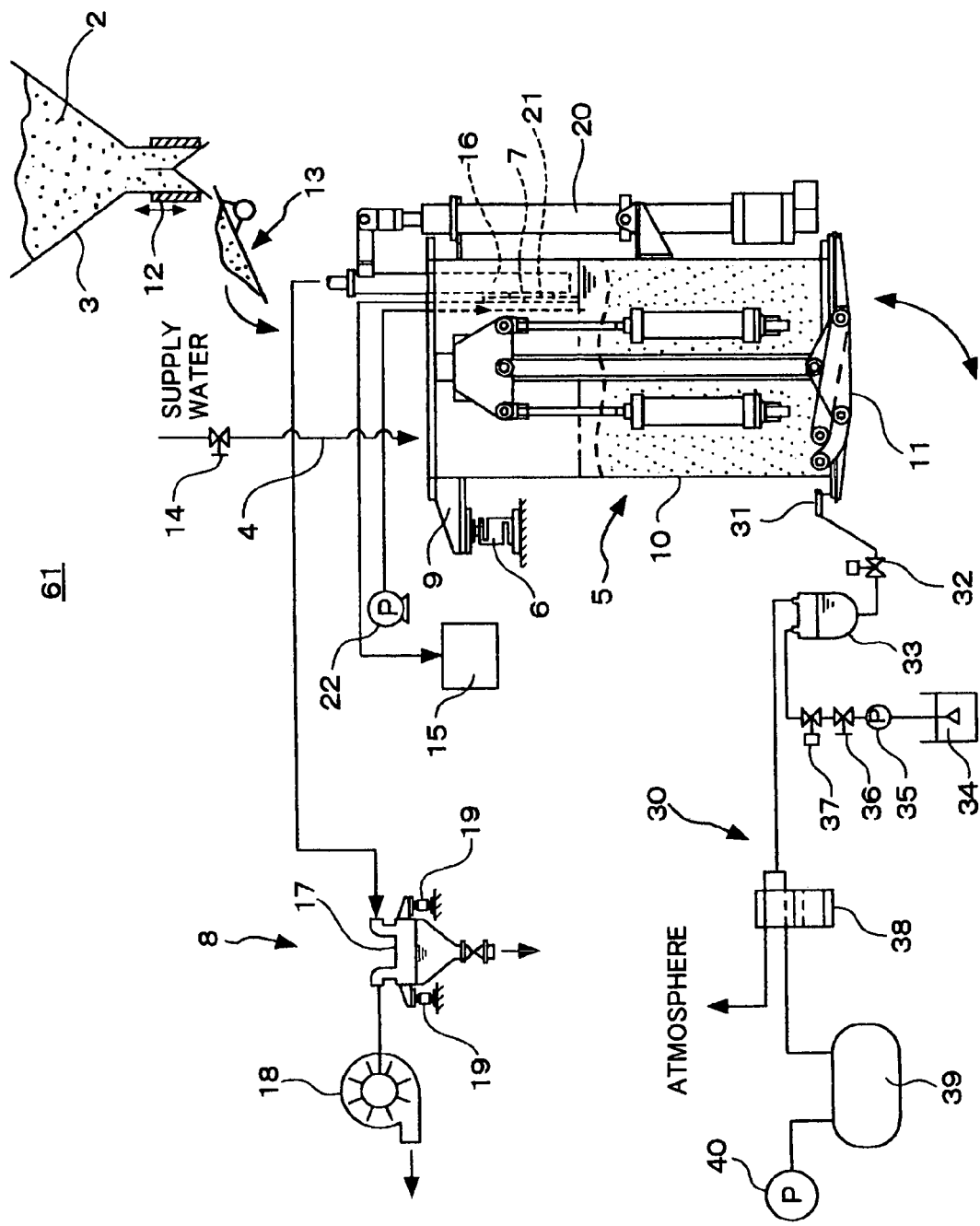

WEIGHING EQUIPMENT FOR CONCRETE MATERIAL

FIELD OF THE INVENTION

The present invention relates to a measuring apparatus for concrete materials for measuring water and aggregate whose surface moisture state is not uniform.

BACKGROUND ART

When kneading concrete materials on site, it is necessary to manage appropriately an amount of water since it has a strong influence on strength of concrete etc. However, a moisture state of the aggregate, which is a concrete material, changes with the storage situations, climatic conditions, and the like. Therefore, if aggregate in wet condition is used, an amount of water in concrete will increase by the amount of surface water of the aggregate. On the other hand, if aggregate in dry condition is used, an amount of water in concrete will decrease by the amount of water absorbed into the aggregate according to an effective absorption of the aggregate.

Therefore, in order to make concrete as specified in a specified mix proportion for maintaining a quality of the concrete, it becomes very important in a case of kneading the concrete to correct the amount of water according to a dryness-and-moisture grade of aggregate.

Referred to as a percentage of surface moisture here is a ratio obtained by dividing mass of the surface water of the aggregate in wet condition (an amount of water adhering to the front face of fine aggregate) by mass of the fine aggregate in the saturated surface-dried condition. Generally aggregate stored, especially fine aggregate is wet in many cases. Therefore, it is common to measure the percentage of surface moisture of the aggregate beforehand as an index of the dryness-and-moisture grade of the aggregate, and to adjust the amount of water based on the percentage of surface moisture measured.

Conventionally, in measurement of such percentage of surface moisture, a small amount of sample has been extracted from a storage container called a stock bin storing fine aggregate for measuring the mass of the sample and the mass of the sample dried completely. Thereafter, the percentage of surface moisture has been computed by using these measured values and the coefficient of water absorption of the aggregate measured beforehand.

However, in such a measuring method, a percentage of surface moisture of aggregate in the stock bin is guessed from a few samples, and therefore accuracy is inferior. On the other hand, in order to measure the mass of aggregate dried completely, heating by a burner or the like is needed. Therefore, it is unreal to measure the mass of aggregate dried completely whose amount is near the actually used amount since much time and expense are needed.

In order to avoid such a problem, an operator checks a kneading situation visually or adjusts the amount of water by using the electric-current value of a mixer. However, these methods have low accuracy primarily. As a result, in order to secure strength of concrete, it is forced to expect a superfluous factor of safety, for example nearly 20%, and it leads to uneconomical mix proportion.

DISCLOSURE OF THE INVENTION

The present invention has been provided in view of the above problems. Therefore, it is an object of the present invention to provide a measuring apparatus for concrete materials capable of measuring mass of aggregate and water correctly.

It is another object of the present invention to provide a measuring apparatus for concrete materials capable of measuring mass of aggregate and water correctly by a water-immersed aggregate measuring method even for concrete of a poor mix with a low slump.

To achieve the above objects, in accordance with a first aspect of the present invention, there is provided a measuring apparatus for concrete materials, comprising: aggregate feed means for feeding aggregate; water supply means; an aggregate measuring bin for storing and measuring aggregate supplied from the aggregate feed means; a measuring tank for storing aggregate supplied from the aggregate feed means as water-immersed aggregate together with water supplied from the water supply means, with a bottom lid capable of maintaining water tightness attached at a bottom opening in such a way as to be free to open or close; water-immersed aggregate mass measuring means for measuring mass of water-immersed aggregate in the measuring tank; water level measuring means for measuring a water level of the water-immersed aggregate in the measuring tank; and water level holding means for absorbing water exceeding a desired water level from the measuring tank to hold the water level of the water-immersed aggregate in the measuring tank at the desired water level and for measuring an amount of the absorbed water, wherein the water level holding means comprises a suction pipe placed so as to move up and down freely, an absorbed water measuring storage tank, which is connected so as to communicate with the suction pipe, for measuring the absorbed water, and suction means connected so as to communicate with the absorbed water measuring storage tank and wherein the aggregate feed means can feed the aggregate to the aggregate measuring bin and the measuring tank.

In accordance with a second aspect of the present invention, there is provided a measuring apparatus for concrete materials, comprising: aggregate feed means for feeding aggregate; water supply means; a measuring tank for storing aggregate supplied from the aggregate feed means as water-immersed aggregate together with water supplied from the water supply means, having a bottom lid capable of maintaining water tightness attached at a bottom opening in such a way as to be free to open or close; water-immersed aggregate mass measuring means for measuring mass of water-immersed aggregate in the measuring tank; water level measuring means for measuring a water level of the water-immersed aggregate in the measuring tank; and water level holding means for absorbing water exceeding a desired water level from the measuring tank to hold the water level of the water-immersed aggregate in the measuring tank at the desired water level and for measuring an amount of the absorbed water, wherein the water level holding means comprises a suction pipe placed so as to move up and down freely, an absorbed water measuring storage tank, which is connected so as to communicate with the suction pipe, for measuring the absorbed water, and suction means connected so as to communicate with the absorbed water measuring storage tank.

In the measuring apparatus for concrete materials according to the first aspect of the invention, there are two types of means for measuring aggregate supplied from the aggregate feed means: the measuring tank for measuring the water-immersed aggregate and the aggregate measuring bin for measuring the aggregate only. The aggregate feed means is arranged in such a way that it can feed the aggregate to the aggregate measuring bin and to the measuring tank.

Therefore, even for concrete whose aggregate is large relative to water, for example, due to a poor mix with a low slump as compared with an ordinary quality of concrete, aggregate to be measured is divided, a certain amount of aggregate is then thrown into the measuring tank and measured as water-immersed aggregate, and the remaining aggregate is directly measured as has been conventional.

More specifically, for the aggregate thrown into the measuring tank together with water, namely, water-immersed aggregate, a water intake at a lower end of the suction pipe is previously positioned so that the water level of the water-immersed aggregate in the measuring tank is held at a desired water level by moving the suction pipe up and down appropriately.

With this arrangement, water exceeding the desired water level as excess water is absorbed by the suction means via the suction pipe after the water-immersed aggregate in the measuring tank reaches the desired water level. Thereby, a volume of the water-immersed aggregate in the measuring tank is held at a predetermined volume. Whether the water level in the measuring tank remains at the desired water level is checked by the water level measuring means separately.

The water absorbed via the suction pipe is stored in the absorbed water measuring storage tank. By measuring the mass of the absorbed water here, a percentage of surface moisture of the aggregate is previously calculated.

On the other hand, the remaining aggregate thrown into the aggregate measuring bin is directly measured as has been conventional as mentioned above. Since an accurate percentage of surface moisture has already been calculated when measured as the water-immersed aggregate, the surface moisture of the aggregate measured as has been conventional can also be estimated with accuracy higher than the conventional one by using the percentage of surface moisture.

In the measuring apparatus for concrete materials according to the second aspect of the invention, the water level holding means comprises the suction pipe placed so as to move up and down freely, an absorbed water measuring storage tank, which is connected so as to communicate with the suction pipe, for measuring absorbed water, and suction means connected so as to communicate with the absorbed water measuring storage tank. Before throwing water and aggregate into the measuring tank, the suction pipe is moved up and down appropriately to position the water intake provided at the lower end of the suction pipe so that the water level of the water-immersed aggregate in the measuring tank is held at the desired water level.

With this arrangement, water exceeding the desired water level as excess water is absorbed by the suction means via the suction pipe after the water-immersed aggregate in the measuring tank reaches the desired water level. Thereby, a volume of the water-immersed aggregate in the measuring tank is held at a predetermined volume.

Whether the water level in the measuring tank remains at the desired water level is checked separately by using the water level measuring means.

The water absorbed via the suction pipe is stored in the absorbed water measuring storage tank. By measuring the mass of the absorbed water at this point, a percentage of surface moisture of the aggregate can be obtained with great accuracy as described later.

If the percentage of surface moisture is previously calculated as mentioned above, it becomes possible to reflect it in the setting of a percentage of surface moisture appropriately in the next measurement.

Although the aggregate is primarily fine aggregate in the above invention, naturally the invention is also applicable to coarse aggregate. While it does not matter whether fine or coarse aggregate is used like this, practically both fine aggregate and coarse aggregates are needed and further it is expected to use a plurality of kinds of fine or coarse aggregates different from one another in density or grading. Particularly, it is often important to make new aggregate having desired grading for convenience in concrete mixing by mixing a plurality of aggregates different in grading at an appropriate proportion.

With the measuring apparatus for concrete materials according to the present invention, it is possible to measure a plurality of aggregates different in at least one of the density and the grading as well as a single kind of aggregate, for example, by a cumulative measuring method.

The term "a plurality of aggregates" concerning the present invention means the aggregates that comprise only fine aggregate, the aggregates that comprise only coarse aggregate, and the aggregates in which fine aggregate and coarse aggregate are arbitrarily mixed. As mentioned above, a plurality of aggregates mean the aggregates whose kinds are different, and all the classification indices about aggregate are contained in the kind of aggregate. The classification indices include density, grading, a place of production, reinforcement, a Young's modulus, durability, distinction of nature, artificiality or byproduct, distinction of beach sand or pit sand, etc.

In addition, when it is written as $\Sigma M_i$ (i=1 to N), it is a summation, i.e., it means $(M_1+M_2+\ldots+M_N)$. When it is written as aggregate of the i-th kind (i=1 to N), it means aggregate of the first kind, aggregate of the second kind, aggregate of the third kind, . . . , and aggregate of the Nth kind.

The measuring tank can be of an arbitrary shape, as long as it can contain water-immersed aggregate. For example, it can be formed in a shape of a hollow cylinder. If it is formed in a shape of a hollow truncated cone, however, a bore of the measuring tank gets larger as it goes below, thereby preventing the water-immersed aggregate from remaining in the measuring tank. Thus, when the measurement is finished, the water-immersed aggregate can be easily taken out of the measuring tank with a free fall of the water-immersed aggregate only by opening the bottom lid of the measuring tank.

If the free fall of the water-immersed aggregate cannot be carried out thoroughly due to aggregate adhesion in the measuring tank inside, the compaction of aggregate, etc., it can be solved by appropriately attaching an oscillating grant instrument such as a vibrator or a knocker in the outside of the measuring tank.

In addition, a predetermined vibrator can be installed above the measuring tank so that it can move up and down freely, and so that it may be buried in the water-immersed aggregate in the measuring tank in the downward location. In this case, by lowering the vibrator and operated during or after the aggregate supply, the aggregate thrown into the measuring tank will be flattened by vibration, thereby preventing aggregate from protruding from the water surface.

A volume of the measuring tank is arbitrary. More specifically, the volume of the measuring tank may be made in agreement with the whole amount required for the unit of concrete mixing, namely, one batch. Otherwise, the volume of the measuring tank can be based on the assumption that measurement is carried out in numbers with one batch divided into some.

The water-immersed aggregate mass measuring means can be, for example, a load cell.

The water level measuring means can be any means as long as it can measure water levels in the measuring tank. If, however, the water level measuring means is an electrode sensor and the electrode sensor is fixed to the suction pipe so that it can move up and down in conjunction with the suction pipe, it becomes possible to omit a device for moving the electrode sensor.

Furthermore, if the electrode sensor is disposed inside a hollow tube and fixed to the suction pipe together with the hollow tube, and further a low-pressure air intake means is provided at an upper end of the hollow tube so that a low-pressure air flows through the hollow tube in a vertical downward direction, bubbles on the water surface in the measuring tank can be removed by the low-pressure air flow, thereby improving a measurement accuracy of the electrode sensor. In addition, by previously positioning the electrode sensor so that a lower end of the hollow tube is slightly immersed in the water of the water-immersed aggregate at a position where a lower end of the electrode sensor is in contact with the surface of the water-immersed aggregate, bubbles removed once are prevented from gathering again at the lower end of the electrode sensor.

Any structure is applicable to the bottom lid, as long as the bottom lid can open or close the bottom opening of the measuring tank body and it can maintain the water tightness in the closed condition. The following arrangement, however, is particularly advantageous as mentioned below. The bottom lid is first coupled to the measuring tank body via predetermined link members so that the bottom lid rotates while moving toward the side of the measuring tank body. A predetermined bottom lid control actuator is then installed in such a way as to be fixed at its lower end on the side face of the measuring tank body. Furthermore, a tip of a piston rod of the bottom lid control actuator is coupled to a tip of an elevator rod pinned at the bottom lid via a predetermined coupling member. The coupling member is then mated with a vertical guide member provided in an extended condition on the side face of the body so that the coupling member can slide freely along the vertical guide member. This arrangement saves a downward space in a height direction needed for opening the bottom lid completely and stabilizes the operation of opening or closing the bottom lid.

In other words, in the conventional technology for the opening or closing operation, if the bottom lid is opened, it will hang down. Therefore, the opening-and-closing space for the bottom lid must be secured in the height direction conventionally. In the present invention, however, it is possible to reduce the downward opening-and-closing space in the height direction. Therefore, the opening at the bottom of the measuring tank body can be lowered correspondingly, and the aggregate can be reliably thrown into a kneading mixer.

Since the bottom lid is coupled to the measuring tank body via two link members having different lengths, the bottom lid rotates so as to turn to the side of the measuring body when the bottom lid is pressed down by the elevator rod. Contrary, when the bottom lid is lifted by the elevator rod, the bottom lid is put in a position substantially parallel to the bottom opening of the measuring tank body immediately before closing the bottom lid. Therefore, a substantially uniform pressure is applied to a seal provided at the bottom opening or the bottom lid. Thereby, uniform water tightness can be secured along the bottom opening, and a partial damage on the seal can be prevented.

In addition, there can be provided washing water spraying means capable of spraying washing water on to the top face of the bottom lid from a washing nozzle attached in the vicinity of the bottom lid. The washing water spraying means comprises a washing water storage tank connected to the washing nozzle, washing water supply means connected to the washing water storage tank, a high-pressure air tank connected so as to communicate with the washing water storage tank via a switching valve, and a compressor connected to the high-pressure air tank. In addition, the switching valve is arranged in such a way that the washing water storage tank communicates with the high-pressure air tank in a first switching position and that the washing water storage tank communicates with atmosphere in a second switching position. In this case, the compressor is previously driven to store a high-pressure air in the high-pressure air tank, and a given amount of washing water is transferred from the washing water supply means to the washing water storage tank in advance. Before the storage of the high-pressure air and the transfer of the washing water, the switching valve is switched to the second switching position where the washing water storage tank communicates with atmosphere, not communicating with the high-pressure air tank.

Subsequently, the water-immersed aggregate that has been measured is discharged to the mixer below with a free fall by opening the bottom lid, and then the switching valve is switched to the first position.

With this operation, the high-pressure air stored in the high-pressure air tank is forced into the washing water storage tank. Thereby, the washing water in the washing water storage tank is sprayed from the washing nozzle with the pressure.

Accordingly, aggregate adhering on the top face of the bottom lid at the time of discharge of the water-immersed aggregate will be washed away and blown off by the washing water. Therefore, when the bottom lid is closed for the next measurement, aggregate is not caught between the measuring tank body and the bottom lid.

Therefore, it is possible to prevent an occurrence of an error in the measurement, which may be caused by a leakage of water from a clearance by aggregate caught between the measuring tank body and the bottom lid. Furthermore, it does not damage the seal members provided in the measuring tank body and the bottom lid.

The following describes a procedure for measuring a plurality of aggregates by using the measuring apparatus for concrete materials according to the present invention. For use of a single kind of aggregate, N should be replaced with 1 in the following description.

First, target mass $M_{di}$ (i=1 to N) is set for water-immersed aggregate at an end of supplying the i-th (i=1 to N) aggregate.

In the first aspect of the present invention, the whole amount of the i-th (i=1 to N) aggregate is not measured as water-immersed aggregate in the measuring tank. The aggregate is divided, for example, equally. One half is measured as water-immersed aggregate in the measuring tank and the other half is measured in the aggregate measuring bin as has been conventional. Therefore, the target mass $M_{di}$ (i=1 to N) of the water-immersed aggregate at the end of supplying the i-th (i=1 to N) aggregate is set, for example, for a half of the aggregate amount.

Subsequently, aggregate of the first kind and water are thrown into the measuring tank so as to obtain water-immersed aggregate in which the aggregate of the first kind does not protrude from the water surface.

When the aggregate and water are thrown into the measuring tank, which should be made to precede is arbitrary. It is, however, preferable to supply the water first and to supply the aggregate next. Thereby, it becomes possible to suppress air bubble mixing in the water-immersed aggregate considerably especially in the case of fine aggregate.

Subsequently, total mass $M_{f1}$ of the water-immersed aggregate is measured. The total mass $M_{f1}$ of the water-immersed aggregate can be measured by subtracting mass of the measuring tank only from mass of the measuring tank filled with the water-immersed aggregate.

Thereafter, mass $M_{a1}$ of the aggregate of the first kind in the saturated surface-dried condition is calculated from the following formula:

$$M_{a1} = \rho_{a1}(M_{f1} - \rho_w \cdot V_{f1})/(\rho_{a1} - \rho_w) \qquad (1)$$

where $\rho_{a1}$ is a density of the aggregate of the first kind in the saturated surface-dried condition, $\rho_w$ is a density of the water, $M_{f1}$ is a total mass of the water-immersed aggregate, and $V_{f1}$ is a total volume of the water-immersed aggregate obtained for the first water level as a preset desired water level.

Subsequently, in the same manner as for the aggregate of the first kind, aggregate of the second kind is supplied to the measuring tank so as not to protrude from the water surface as water-immersed aggregate, and then a total mass $M_{f2}$ of the water-immersed aggregate is measured.

Thereafter, mass $M_{a2}$ of the aggregate of the second kind in the saturated surface-dried condition is calculated from the following formula:

$$M_{a2} = \rho_{a2}((M_{f2} - M_{a1}) - \rho_w(V_{f2} - M_{a1}/\rho_{a1}))/(\rho_{a2} - \rho_w) \qquad (2)$$

where $\rho_{a1}$ is the density of the aggregate of the first kind in the saturated surface-dried condition, $\rho_{a2}$ is a density of the aggregate of the second kind in the saturated surface-dried condition, $\rho_w$ is a density of the water, $M_{f2}$ is a total mass of the water-immersed aggregate, and $V_{f2}$ is a total volume of the water-immersed aggregate obtained for the second water level as a preset desired water level.

Hereinafter, the above procedure is repeated for the sequential calculation up to the mass $M_{a(N-1)}$ of aggregate of the (N-1)th kind in the saturated surface-dried condition. Thereafter, the aggregate of the Nth kind is supplied to the measuring tank so as to obtain water-immersed aggregate in which the aggregate of the Nth kind does not protrude from the water surface.

Subsequently, the total mass $M_{fN}$ of the water-immersed aggregate is measured in the same manner as for the above.

Thereafter, mass $M_{aN}$ of the aggregate of the Nth kind in the saturated surface-dried condition and the mass of water $M_w$ are calculated from the following formulas:

$$M_{aN} = \rho_{aN}((M_{fN} - \Sigma M_{ai}(i=1 \text{ to } (N-1))) - \rho_w(V_{fN} - \Sigma(M_{ai}/\rho_{ai})(i=1 \text{ to } (N-1))))/(\rho_{aN} - \rho_w) \qquad (3)$$

$$M_w = \rho_w(\rho_{aN}(V_{fN} - \Sigma(M_{ai}/\rho_{ai})(i=1 \text{ to } (N-1))) - (M_{fN} - \Sigma M_{ai}(i=1 \text{ to } (N-1))))/(\rho_{aN} - \rho_w) \qquad (4)$$

where $\rho_{ai}$ (i=1 to N) is a density of aggregate of the i-th kind (i=1 to N) in the saturated surface-dried condition, $\rho_w$ is a density of the water, $M_{fN}$ is a total mass of the water-immersed aggregate, and $V_{fN}$ is a total volume of the water-immersed aggregate obtained for the Nth water level as a preset desired water level.

When the aggregate of the i-th kind (i=1 to N) is cumulatively supplied to the measuring tank, the aggregate of the i-th kind (i=1 to N) is supplied to the measuring tank continuously or intermittently at a predetermined rate, while the total mass $M_{fi}$ (i=1 to N) of the water-immersed aggregate is measured in real time or at predetermined time intervals. During the supply of aggregate of the j-th kind among the aggregate of the i-th kind (i=1 to N), excess water is absorbed to prevent the water level of the water-immersed aggregate at that time from exceeding the preset j-th water level. When the total mass $M_{fj}$ of the water-immersed aggregate has reached the target mass $M_{dj}$ of the water-immersed aggregate, the supply of the aggregate of the j-th kind is ended.

On the other hand, if it is confirmed with the water level measuring means that the water of the water-immersed aggregate at that time does not reach the preset j-th water level, water is added to the measuring tank so that it reaches the j-th water level. Thereafter, the total mass $M_{fj}$ of the water-immersed aggregate is measured again and recalculation is made for the mass $M_{aj}$ of the aggregate of the j-th kind in the saturated surface-dried condition and for the mass $M_w$ of the water.

If there remains any aggregate to be cumulatively supplied subsequently, in other words, if there is any aggregate other than the last one among a plurality of aggregates to be cumulatively supplied, aggregate of the (j+1)th kind is supplied continuously in the same manner as for the above.

After measuring the aggregate of the i-th kind (i=1 to N) and water as mentioned above, the amounts of other concrete materials such as cement and a chemical admixture are measured appropriately. Thereafter, the aggregate and water are thrown into the kneading mixer and kneaded together with these concrete materials. During this operation, if the total mass $M_{fj}$ of the water-immersed aggregate has reached the target mass $M_{dj}$ of the water-immersed aggregate while excess water is drained to prevent the water of the water-immersed aggregate from exceeding the preset j-th water level, the mass $M_{ai}$ (i=1 to N) of the i-th aggregate in the saturated surface-dried condition becomes equal to the value set up first, and therefore the field mix need not be corrected.

On the other hand, if the water of the water-immersed aggregate does not reach the preset j-th water level, water is added so that it reaches the j-th water level. Therefore, the measured value of the mass $M_{aj}$ of the aggregate of the j-th kind in the saturated surface-dried condition differs from the value set up first. In this case, the result of the measurement is compared with the field mix initially set according to the specified mix proportion, and the field mix is corrected, if necessary. More specifically, the measured mass of the aggregate is compared with the mass of aggregate of the field mix set up first, and the mixing volume of one batch is corrected according to the ratio obtained by the comparison. Furthermore, according to this ratio, water is added to supply the deficiency of water as secondary water, or excess water is drained. Similarly, also about the amounts of other concrete materials such as cement and a chemical admixture, the initial field mix is corrected according to the ratio mentioned above and other concrete materials are measured according to the correction, and then these are thrown into the kneading mixer and kneaded.

In the first aspect of the present invention, as mentioned above, the percentage of surface moisture of aggregate is calculated for each aggregate in the following procedure in addition to the measurement of the aggregate and water. More specifically, the amount of supplied water $M_I$ to the measuring tank is previously measured, and the percentage of surface moisture of the aggregate is calculated by using an accumulation value of the amount of absorbed water $M_O$ from the measuring tank measured by the absorbed water measuring storage tank.

Concretely, the amount of supplied water $M_I$ to the measuring tank, the amount of absorbed water $M_O$ from the measuring tank, and the total mass $M_{fi}$ (i=1 to N) are substituted for the following formula to obtain $\Sigma M_{awj}$ (j=1 to i):

$$\Sigma M_{awj}(j=1 \text{ to } i) = M_{fi} - (M_I - M_O) \quad (5)$$

$M_{awi}$ is then calculated from the following formula:

$$M_{awi} = \Sigma M_{awj}(j=1 \text{ to } i) - \Sigma M_{awj}(j=1 \text{ to } (i-1)) \quad (6)$$

Thereafter, $M_{awi}$ is substituted for the following formula and a percentage of surface moisture is calculated:

$$(M_{awi} - M_{ai})/M_{ai} \quad (7)$$

The accumulation value of the amount of supplied water $M_I$ to the measuring tank does not necessarily increase, but can be the amount of water thrown first. In other words, the accumulation value can be fixed without change. Similarly, water is not necessarily absorbed by the amount of the absorbed water $M_O$ from the measuring tank, but the accumulation value may remain zero.

Subsequently, a measured value of the remaining aggregate after the reduction is corrected by using the percentage of surface moisture calculated as mentioned above.

Also in the second aspect of the present invention, if the amount of supplied water $M_I$ to the measuring tank is previously measured, the percentage of surface moisture of aggregate can be calculated accurately by using the accumulation value of the amount of absorbed water $M_O$ from the measuring tank measured in the absorbed water measuring storage tank in the same manner as for the above.

Thus, with measuring the aggregate as water-immersed aggregate, the surface moisture of aggregate is indirectly calculated as a part of mass $M_w$ of water in consideration of variation of aggregates whose moisture state is not uniform. Furthermore, the mass of aggregate is calculated as the mass $M_{ai}$ (i=1 to N) of the aggregate in the saturated surface-dried condition. In other words, the mass of the aggregate and the water are calculated on the conditions equivalent to the specified mix proportion. Therefore, even if the humidity grade of the aggregate is not fixed at every measurement, it is possible to make concrete according to the specified mix proportion.

Furthermore, when the total mass $M_{fj}$ of the water-immersed aggregate has reached the target mass $M_{dj}$ of the water-immersed aggregate, the supply of the aggregate of the j-th kind is ended. If the water of the water-immersed aggregate does not reach the preset j-th water level at that time, water is added so as to reach the j-th water level. Thereafter, the total mass $M_{fj}$ of the water-immersed aggregate is measured again and recalculation is made for the mass $M_{aj}$ of the aggregate of the j-th kind in the saturated surface-dried condition and for the mass $M_w$ of the water. According to the above process, the total volume $V_{fi}$ (i=1 to N) of the water-immersed aggregate becomes a known value and therefore it need not be measured. Furthermore, it leads to a correct management of the input of the aggregate of the i-th kind (i=1 to N). As a result, it becomes possible to make concrete according to the specified mix proportion.

In addition, a plurality of aggregates different from one another in density, grading, or the like can be measured efficiently and very accurately within a single measuring tank, while accurately calculating the effects of the surface moisture caused by differences in the moisture state as a part of the final amount of water.

When taking into consideration the air content in the water-immersed aggregate (a %), still more accurate measurement can be performed with the actual total volume by replacing $V_{fi}$ (i=1 to N) with $V_{fi}$ (i=1 to N)·(1−a/100).

Furthermore, in the first aspect of the present invention, with an application of a percentage of surface moisture calculated at the time of measuring the aggregate as water-immersed aggregate, a measured value can be corrected accurately by a conventional measuring method with an aggregate measuring bin.

BRIEF DESCRIPTION OF THE DRAWINGS

FIG. 4 is a general view of a preferable measuring apparatus for concrete materials according to a second embodiment of the present invention.

BEST MODE FOR CARRYING OUT THE INVENTION

Hereinafter, preferred embodiments of a measuring apparatus according to the present invention will be described below by using the accompanying drawings.

[First Embodiment]

Figure 1:
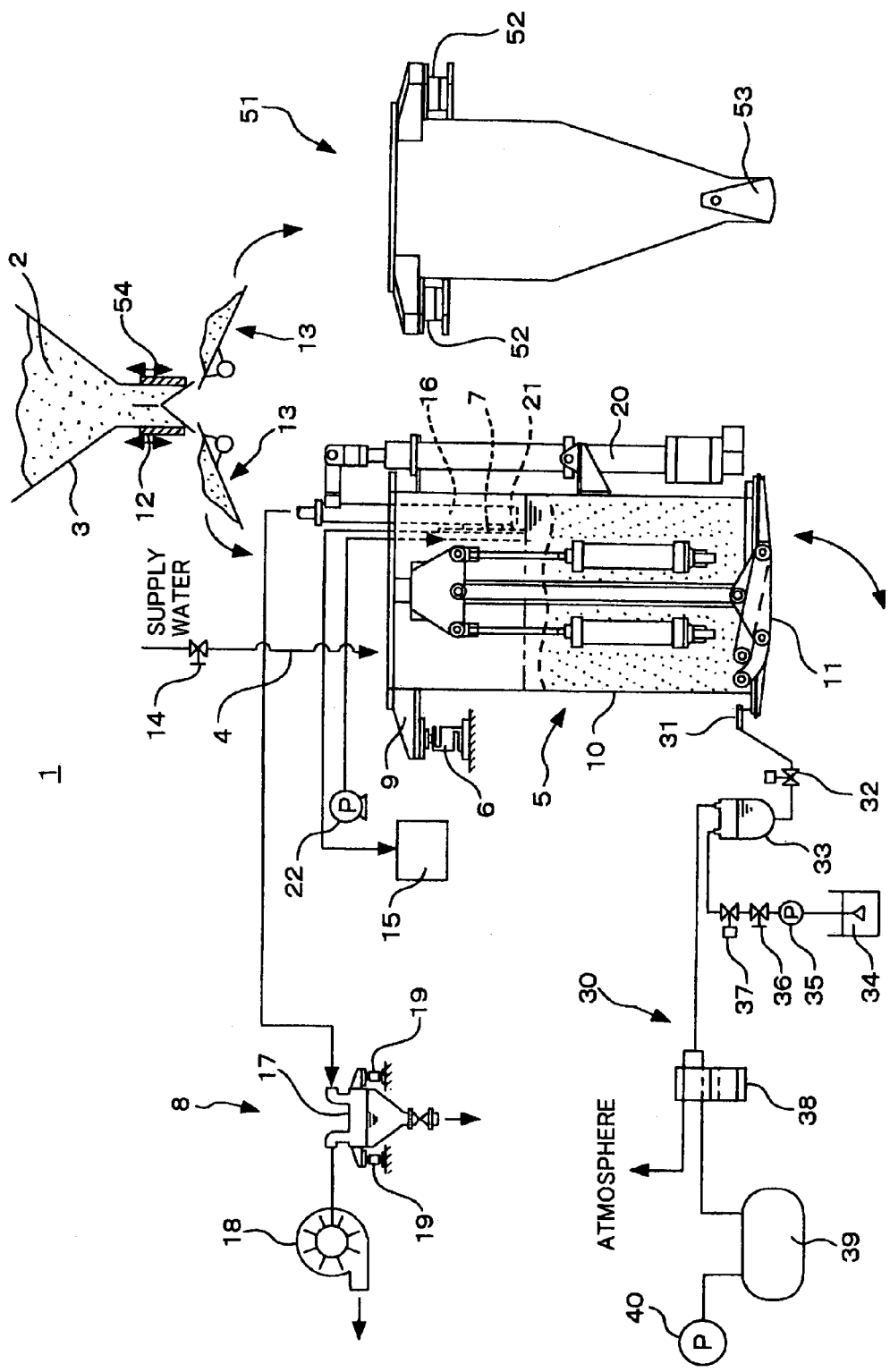
FIG. 1 is a general view of a preferable measuring apparatus for concrete materials according to a first embodiment of the present invention.

Referring to FIG. 1, there is shown a general view of a measuring apparatus for concrete materials according to the first embodiment. As shown in FIG. 1, the measuring apparatus 1 for concrete materials according to the embodiment generally comprises: an aggregate hopper 3 as aggregate feed means for feeding fine aggregate 2 as aggregate; a water supply pipe 4 as water supply means; an aggregate measuring bin 51 for storing and measuring the fine aggregate 2 supplied from the aggregate hopper 3; a measuring tank 5 for storing the fine aggregate 2 supplied from the aggregate hopper 3 as water-immersed aggregate together with water supplied through the water supply pipe 4; a load cell 6 as water-immersed aggregate mass measuring means for measuring mass of the water-immersed aggregate in the measuring tank; an electrode sensor 7 as water level measuring means for measuring the water level of the water-immersed aggregate in the measuring tank; and a water level holding device 8 as water level holding means for holding the water level of the water-immersed aggregate in the measuring tank 5 at a desired water level.

The aggregate hopper 3 and the load cell 6 are attached each to a stand not shown, and a support bracket 9 of the measuring tank 5 is put on the load cell so that the measuring tank 5 is held in a suspended condition. Thereby, mass of the measuring tank can be measured by the load cell 6. It is preferable to place the load cell 6, for example, in three places at 120° intervals on the same horizontal surface so that the measuring tank 5 can be held in a stable and suspended condition during measurement.

Similarly, the aggregate measuring bin 51 is put on a load cell 52 attached to a stand, which is not shown, so that the aggregate measuring bin 51 is held in a suspended condition.

With this arrangement, the mass of the aggregate measuring bin 51 can be measured with the load cell 52. Under the aggregate measuring bin 51, a bottom lid 53 of a swiveling type is provided. By swiveling the bottom lid laterally, aggregate is thrown into a mixer not shown when the measurement is finished.

The measuring tank 5 comprises a measuring tank body 10 formed in a shape of a hollow truncated cone so that a bore of the body gets larger as it goes below and a bottom lid 11 for covering the bottom opening of the measuring tank body in a condition where it can maintain water tightness in such a way as to be free to open or close. Thus, when the measurement is finished, the water-immersed aggregate drops down with a free fall only by opening the bottom lid 11, not having remaining aggregate in the measuring tank, without an oscillating instrument such as a vibrator. Thereafter, it can be thrown into a kneading mixer not shown together with cement or coarse aggregate measured separately.

A volume of the measuring tank 5 is arbitrary. It may be made in agreement with the whole amount required for the unit of concrete mixing, namely, one batch. Otherwise, the volume of the measuring tank 5 can be based on the assumption that measurement is carried out in numbers with one batch divided into some.

For the opening at the lower end of the aggregate hopper 3, there is provided an elevating gate 12 working with the load cell 6. The supply of the fine aggregate 2 to the measuring tank 5 is stopped by closing the elevating gate 12 according to a mass value measured by the load cell 6.

Under the opening at the lower end of the aggregate hopper 3, there is provided a vibrating feeder 13 having an electromagnetic vibrator extending to the upper opening of the measuring tank 5. The fine aggregate 2 is conveyed from under the aggregate hopper 3 to the upper opening of the measuring tank 5 by using the vibrating feeder, thereby preventing granulation and therefore preventing mixing of air bubbles.

Similarly, for the opening at the lower end of the aggregate hopper 3, there is provided an elevating gate 54 working with the load cell 52. The supply of the fine aggregate 2 to the aggregate measuring bin 51 is stopped by closing an elevating gate 54 according to a mass value measured by the load cell 52. Furthermore, under the opening at the lower end of the aggregate hopper 3, there is provided a vibrating feeder 13 having an electromagnetic vibrator extending to the upper opening of the aggregate measuring bin 51. The fine aggregate 2 is conveyed from under the aggregate hopper 3 to the upper opening of the aggregate measuring bin 51 by using the vibrating feeder, thereby preventing granulation and therefore preventing mixing of air bubbles.

The water supply pipe 4 is provided with a water supply valve 14. The water supply processing to the measuring tank 5 is carried out with opening or closing the water supply valve.

The electrode sensor 7 is connected to a self-powered sensor controller 15. It can measure the water level of water-immersed aggregate by monitoring changes in an energized condition when its lower end is put in contact with the water surface of the water-immersed aggregate in the measuring tank 5. In this event, one electrode terminal of a power supply, which is not shown, incorporated in the sensor controller 15 is electrically connected to the electrode sensor 7, and the other electrode terminal is electrically connected to the measuring tank 5 made of, for example, steel.

The water level holding device 8 comprises a suction pipe 16 placed so as to move up and down freely, an absorbed water measuring storage tank 17, which is connected so as to communicate with the suction pipe, for measuring absorbed water, and a suction fan 18 as suction means connected so as to communicate with the absorbed water measuring storage tank. Thereby, the absorbed water measuring storage tank 17 can measure the mass of water absorbed by load cell 19.

The suction pipe 16 is coupled to a piston rod of a suction pipe elevation actuator 20 attached to the side face of the measuring body 10. Thereby, the suction pipe can be moved up and down freely by driving the suction pipe elevation actuator. For the suction pipe elevation actuator 20, it is preferable to use, for example, an electric servo cylinder, to secure the precision in elevation.

Figure 2A:
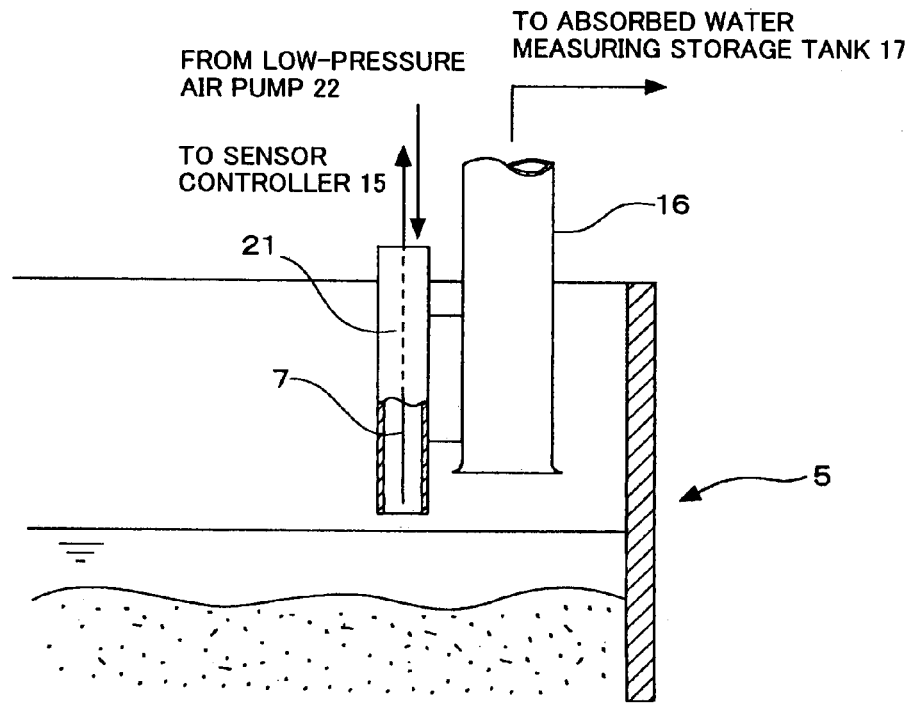
FIG. 2 is a diagram showing actions of an electrode sensor 7, a hollow tube 21 where the sensor is disposed, and a suction pipe 16.

The above electrode sensor 7 is disposed inside a hollow tube 21 and the hollow tube is fixed to the suction pipe 16, as apparent from FIG. 2(a). More specifically, the hollow tube 21 and the electrode sensor 7 disposed inside it are arranged so as to move up and down by using the suction pipe elevation actuator 20, working with the suction pipe 16.

On the other hand, the hollow tube 21 is connected at its upper end to a low-pressure air pump 22 as low-pressure air intake means, for example, via a vinyl tube. Thereby, a low-pressure air flows through the hollow tube 21 in a vertical downward direction by driving the low-pressure air pump 22.

Figure 3:
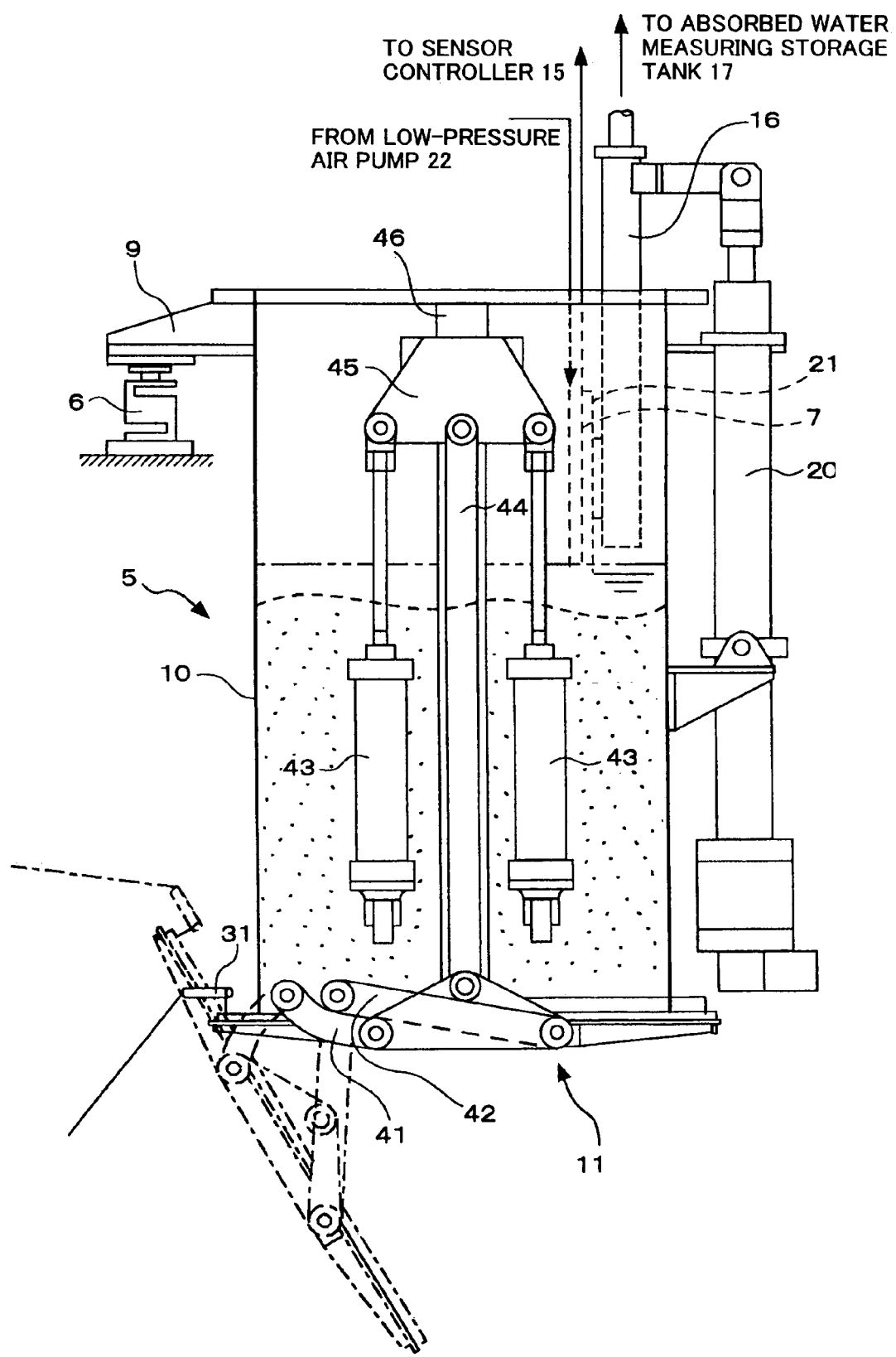
FIG. 3 is a detailed side view of a measuring tank.

The bottom lid 11 is coupled to the side face of the measuring tank body 10 via a shorter link member 41 and a link member 42 longer than the link member 41, as apparent from FIG. 3. Thereby, when the bottom lid is pressed down, it can rotate turning to the side of the measuring tank body 10 due to a smaller radius of gyration of the link member 41 and a larger radius of gyration of the link member 42.

Furthermore, bottom lid control actuators 43, 43 are placed so that they can be fixed to the side face of the measuring tank body 10 at the lower end. A tip of a piston rod of the bottom lid control actuator is coupled to a tip of an elevator rod 44 pinned to the bottom lid 11 via a coupling member 45. The coupling member 45 is mated with a vertical guide 46 so that it can slide freely along the vertical guide 46 provided in an extended condition on the side face of the measuring tank body 10.

The vertical guide 46 can be formed by welding, for example, a steel product having a T-shaped cross section vertically to the side face of the measuring tank body 10.

On the other hand, the measuring apparatus 1 for concrete materials according to this embodiment is provided with a washing water spraying device 30 as washing water spraying means for spraying washing water on the top face of the bottom lid 11. As apparent from FIG. 1 and FIG. 3, the washing water spraying device comprises a washing nozzle 31 attached in the vicinity of the bottom lid 11, a washing water storage tank 33 connected to the washing nozzle 31 via a washing valve 32, a washing water supply tank 34, a high-pressure air tank 39 connected so as to communicate with the washing water storage tank 33 via a switching valve 38, and a compressor 40 connected to the high-pressure air tank. The washing water supply tank 34 is connected to the washing water storage tank 33 via a washing water supply valve 37, a flow regulating valve 36 and a washing water pump 35. The water supply tank 34, the washing water supply valve 37, the flow control valve 36 and the washing water pump 35 constitute washing water supply means. The switching valve 38 is arranged in such a way that the washing water storage tank 33 communicates with the high-pressure air tank 39 in a first switching position and that the washing water storage tank 33 communicates with atmosphere in a second switching position.

In the measuring apparatus 1 for concrete materials according to this embodiment, there are two types of means for measuring the fine aggregate 2 supplied from the aggregate hopper 3: the measuring tank 5 for measuring water-immersed aggregate and the aggregate measuring bin 51 for measuring only the fine aggregate. The aggregate hopper 3 is arranged in such a way that it can feed the fine aggregate 2 to the aggregate measuring bin 51 and to the measuring tank 5 individually.

Therefore, even for concrete whose aggregate is large relative to water, for example, due to a poor mix with a low slump as compared with an ordinary quality of concrete, aggregate to be measured is divided and a certain amount of aggregate is then thrown into the measuring tank and measured as water-immersed aggregate. Thereafter, the remaining aggregate is directly measured as has been conventional.

More specifically, for the fine aggregate supplied to the measuring tank 5 together with water, namely, water-immersed aggregate, a water intake at a lower end of the suction pipe 16 is previously positioned so that the water level of the water-immersed aggregate in the measuring tank 5 is held at a desired water level by driving the suction pipe elevation actuator 20 to move the suction pipe 16 up and down appropriately. In connection with the positioning, the distance between the water intake of the suction pipe 16 and the desired water level can be appropriately determined by experiment or the like.

With the positioning of the water intake of the suction pipe 16, water exceeding the desired water level as excess water is absorbed by the suction fan 18 via the suction pipe 16 after the water-immersed aggregate in the measuring tank 5 reaches the desired water level. Thereby, a volume of the water-immersed aggregate in the measuring tank 5 is held at a predetermined volume.

Whether the water level in the measuring tank 5 remains at the desired water level is checked separately by using the electrode sensor 7 as water level measuring means.

The water absorbed via the suction pipe 16 is stored in the absorbed water measuring storage tank 17. At this point, a percentage of surface moisture of the fine aggregate 2 is previously calculated by measuring the mass of the absorbed water.

On the other hand, the remaining aggregate thrown into the aggregate measuring bin 51 is directly measured as has been conventional as mentioned above. Since an accurate percentage of surface moisture has already been calculated when measured as the water-immersed aggregate, the surface moisture of the aggregate measured as has been conventional can also be estimated with accuracy higher than the conventional one by using the percentage of surface moisture.

The following describes a procedure for measuring the fine aggregate 2 by using the measuring apparatus 1 for concrete materials according to this embodiment, on the assumption that the fine aggregate 2 comprising two kinds of fine aggregates A and B is divided and that one of the aggregates divided is supplied to the measuring tank 5 and the other aggregate is supplied to the aggregate measuring bin 51 sequentially.

First, target mass $M_{di}$ (i=1, 2) is set for water-immersed aggregate at an end of supplying the fine aggregate A and the fine aggregate B. As mentioned above, the whole amount of the i-th (i=1 to N) aggregate is not measured as water-immersed aggregate in the measuring tank. Instead, the aggregate is divided, for example, equally, and one half is measured as water-immersed aggregate in the measuring tank 5 and the other half is measured in the aggregate measuring bin 51 as has been conventional. Therefore, the target mass $M_{di}$ (i=1 to N) of the water-immersed aggregate at the end of supplying the i-th (i=1 to N) aggregate is set, for example, for a half of the aggregate amount.

To set the target mass $M_{di}$ (i=1, 2), first, set filling factor F of the water-immersed aggregate, which is a volume ratio of the fine aggregate to the total volume of the divided fine aggregate and water, and then set the mixing volume $N_0$ of one batch. Furthermore, set the volume of the fine aggregate on the basis of the filling factor F of the water-immersed aggregate and the mixing volume $N_0$ of one batch. Thereafter, target input mass of the fine aggregate A and the fine aggregate B in the saturated surface-dried condition is determined based on the mix proportion of the fine aggregate A and the fine aggregate B and densities of the fine aggregate A and the fine aggregate B in the saturated surface-dried condition. Subsequently, the mass of the fine aggregate A and the water supplied first (primary measured water), into which the fine aggregate A has been thrown, is determined as target mass $M_{d1}$ of the water-immersed aggregate. The mass of the fine aggregate B and the water-immersed aggregate, which include the fine aggregate A and the primary measured water, is determined as target mass $M_{d2}$ of water-immersed aggregate which include the fine aggregate A, B and the primary measured water. Before the determination of the target mass $M_{di}$ (i=1, 2) of the water-immersed aggregate, preferably set the most appropriate percentage of surface moisture and include surface water of the fine aggregate A, B in the primary measured water. It is effective to reduce the correction after the measurement.

Subsequently, the fine aggregate A and water are thrown into the measuring tank 5 so as to obtain water-immersed aggregate in which the fine aggregate does not protrude from the water surface. When the fine aggregate A and the water are thrown into the measuring tank, it is preferable to supply the water first and to supply the aggregate next in order to suppress air bubble mixing in the water-immersed aggregate. Furthermore, instead of throwing the fine aggregate A into the measuring tank 5 directly, preferably the fine aggregate A is conveyed to the measuring tank 5 by using the vibrating feeder 13 with an electromagnetic vibrator, as shown in FIG. 1. Thereby, it becomes possible to prevent granulation of the fine aggregate and therefore to prevent the mixing of air bubbles.

Before throwing the water and the fine aggregate A into the measuring tank 5, the suction pipe 6 of the water-level holding device 8 is appropriately moved up and down to position the water intake, which is provided at the lower end of the suction pipe 16, so that the water level of the water-immersed aggregate in the measuring tank 5 is held at the first water level as a desired water level.

Subsequently, total mass $M_{f1}$ of the water-immersed aggregate is measured with the load cell 6. The total mass $M_{f1}$ of the water-immersed aggregate can be measured by subtracting the mass of the measuring tank 5 only from the mass of the measuring tank 5 filled with the water-immersed aggregate.

In measuring the total mass $M_{f1}$ of the water-immersed aggregate, the fine aggregate A is supplied continuously or intermittently at a predetermined rate, while the total mass $M_{f1}$ of the water-immersed aggregate is measured in real time or at predetermined time intervals. During the supply of the fine aggregate A, excess water is absorbed by using the water level holding device 8 to prevent the water level of the water-immersed aggregate from exceeding the preset first water level as a desired water level. When the total mass $M_{f1}$ of the water-immersed aggregate has reached the target mass $M_{d1}$ of the water-immersed aggregate, the supply of the fine aggregate A is ended.

Since the elevating gate 12 provided in the opening at the lower end of the aggregate hopper 3 is linked with the load cell 6, the elevating gate 12 is closed in response to a control signal from the load cell 6 when the total mass $M_{f1}$ of the water-immersed aggregate has reached the target mass $M_{d1}$ of the water-immersed aggregate, by which the supply of the fine aggregate A is automatically stopped.

Figure 2B:
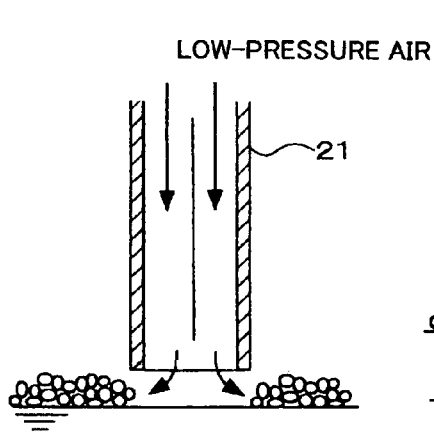
Figure 2C:
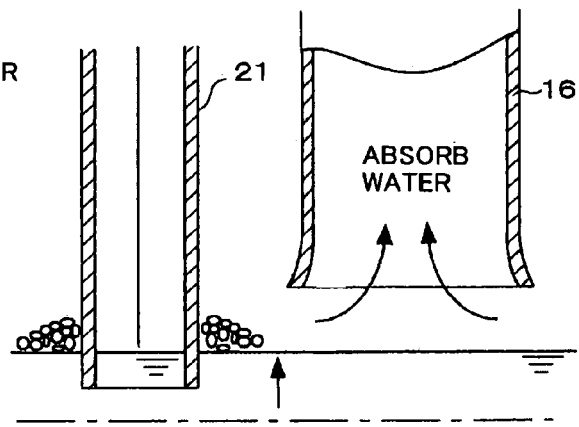

Furthermore, it is checked that the water level at the end of the supply has reached the first water level separately by using the electrode sensor 7. When the water level increases due to the supply of the fine aggregate A and is coming close to the first water level, the low-pressure air pump 22 is operated to feed a low-pressure air into the hollow tube 21. Thereby, as shown in FIG. 2(b), bubbles on the water surface of the water-immersed aggregate are blown away to the outside of the hollow tube 21. Therefore, when the water level of the water-immersed aggregate in the measuring tank 5 has reached the first water level, the water level can be precisely detected by the electrode sensor 7, not being disturbed by bubbles on the surface of the water-immersed aggregate, as shown in FIG. 2(c).

Subsequently, mass $M_{a1}$ of the fine aggregate A in the saturated surface-dried condition is calculated from the following formula:

$$M_{a1}=\rho_{a1}(M_{f1}-\rho_w \cdot V_{f1})/(\rho_{a1}-\rho_w) \quad (1)$$

where $\rho_{a1}$ is a density of the fine aggregate A in the saturated surface-dried condition, $\rho_w$ is a density of the water, $M_{f1}$ is a total mass of the water-immersed aggregate, and $V_{f1}$ is a total volume of the water-immersed aggregate obtained for the preset first water level.

On the other hand, when the total mass $M_{f1}$ of the water-immersed aggregate has reached the target mass $M_{d1}$ of the water-immersed aggregate, if it is confirmed with the electrode sensor 7 that the water of the water-immersed aggregate does not reach the preset first water level, water is added so that it reaches the first water level. Thereafter, the total mass $M_{f1}$ of the water-immersed aggregate is measured again and recalculation is made for the mass $M_{a1}$ of the fine aggregate A in the saturated surface-dried condition.

Thereafter, the fine aggregate B is thrown into the measuring tank 5 so as to obtain water-immersed aggregate in which the fine aggregate does not protrude from the water surface similarly to the fine aggregate A.

In other words, similarly the suction pipe 16 is appropriately moved up and down previously to position the water intake provided at the lower end of the suction pipe 16 so that the water level of the water-immersed aggregate in the measuring tank 5 is held at the second water level as a desired water level.

The total mass $M_{f2}$ of the water-immersed aggregate is measured, next. In measuring the total mass $M_{f2}$ of the water-immersed aggregate, similarly to the fine aggregate A, the fine aggregate B is supplied continuously or intermittently at a predetermined rate, while the total mass $M_{f2}$ of the water-immersed aggregate is measured in real time or at predetermined time intervals. During the supply of the fine aggregate B, excess water is absorbed by using the water level holding device 8 to prevent the water level of the water-immersed aggregate from exceeding the preset second water level as a desired water level. When the total mass $M_{f2}$ of the water-immersed aggregate has reached the target mass $M_{d2}$ of the water-immersed aggregate, the supply of the fine aggregate B is ended.

Similarly to the fine aggregate A, it is checked that the water level at the end of the supply has reached the second water level separately by using the electrode sensor 7. When the water level increases due to the supply of the fine aggregate B and is coming close to the second water level, the low-pressure air pump 22 is operated to feed an low-pressure air into the hollow tube 21. Thereby, the water level can be precisely detected by the electrode sensor 7, not being disturbed by bubbles on the surface of the water-immersed aggregate as mentioned above.

Subsequently, mass $M_{a2}$ of the fine aggregate B in the saturated surface-dried condition and mass of water $M_w$ are calculated from the following formulas:

$$M_{a2}=\rho_{a2}((M_{f2}-\Sigma M_{ai}(i=1,\ 2))-\rho_w(V_{f2}-\Sigma(M_{ai}/\rho_{ai})(i=1,\ 2)))/(\rho_{a2}-\rho_w) \quad (3)$$

$$M_w=\rho_w(\rho_{a2}(V_{f2}-\Sigma(M_{ai}/\rho_{ai})(i=1,\ 2))-(M_{f2}-\Sigma M_{ai}(i=1,\ 2)))/(\rho_{a2}-\rho_w) \quad (4)$$

where $\rho_{a1}$ is a density of the fine aggregate A in the saturated surface-dried condition, $\rho_{a2}$ is a density of the fine aggregate B in the saturated surface-dried condition, $\rho_w$ is a density of the water, $M_{f2}$ is a total mass of the water-immersed aggregate, and $V_{f2}$ is a total volume of the water-immersed aggregate obtained for the preset second water level.

On the other hand, when the total mass $M_{f2}$ of the water-immersed aggregate has reached the target mass $M_{d2}$ thereof and if it is confirmed with the electrode sensor 7 that the water of the water-immersed aggregate does not reach the preset second water level, water is added so that it reaches the second water level. Thereafter, the total mass $M_{f2}$ of the water-immersed aggregate is measured again and recalculation is made for the mass $M_{a2}$ of the fine aggregate B in the saturated surface-dried condition and for the mass $M_w$ of the water.

After measuring the fine aggregate A, the fine aggregate B, and the water in this manner, the result of the measurement is compared with the initial field mix set according to the specified mix proportion, and the field mix is corrected, if necessary.

More specifically, if the total mass $M_{fi}$ (i=1, 2) of the water-immersed aggregate reaches the target mass $M_{d2}$ of the water-immersed aggregate while excess water is absorbed to prevent the water-immersed aggregate from exceeding the first and second water levels, the total mass $M_{fi}$ (i=1, 2) of the water-immersed aggregate and the total volume $V_{fi}$ (i=1, 2) of the water-immersed aggregate are equal to the values set up first. In this case, the field mix need not be corrected. Therefore, the water-immersed aggregate is directly thrown into the kneading mixer together with other concrete materials and kneaded.

On the other hand, the level of the water-immersed aggregate does not reach the preset first and second water levels, water is added so that it reaches the first and second water levels. As a result, the total mass $M_{fi}$ (i=1, 2) of the re-measured water-immersed aggregate, and thus the mass of the fine aggregate A and the mass of the fine aggregate B in the saturated surface-dried condition calculated from the total mass $M_{fi}$ (i=1, 2) are different from the values set up first.

Therefore, in this case, the mass of the measured fine aggregate A and that of the fine aggregate B are compared with the mass of the fine aggregate A and that of the fine aggregate B of the field mix set up initially to calculate a ratio of a mass summation of the measured fine aggregate A and fine aggregate B in the saturated surface-dried condition to a mass summation of the preset fine aggregate A and fine aggregate B in the saturated surface-dried condition. For example, if it is 0.9, the mass of the measured fine aggregate A and fine aggregate B is 10% less than the preset value. Therefore, the mixing volume of one batch $N_0$ itself need be decreased by 10% to get $0.9 \cdot N_0$. Accordingly, the ratio is also applied to other concrete materials such as cement and a chemical admixture to correct the initial field mix and re-measure according to the corrected filed mix. For the water, similarly the preset amount of water is compared with the measured amount of water. Water is then added to supply the deficiency of water as secondary water, or excess water is drained. Thereafter, these concrete materials are thrown into the kneading mixer and kneaded.

To open the bottom lid 11 to take out the water-immersed aggregate that has been measured, drive the bottom lid control actuators 43, 43, first, to retract the piston rod as shown in FIG. 3.

With this operation, the coupling member 45 pinned with the piston rod slides downward along the vertical guide 46 provided in an extended condition on the side face of the measuring tank body 10, and with the motion the elevator rod 44 pinned with the coupling member presses down the bottom lid 11.

On the other hand, when the pressing force with the elevator rod 44 acts on the bottom lid 11, the bottom lid 11 rotates so as to turn to the side of the measuring tank body 10 as indicated by a dashed line in FIG. 3 and the water-immersed aggregate in the measuring tank 5 drops down from the bottom opening of the measuring tank body 10.

After throwing the measured water-immersed aggregate into the mixer, the bottom lid 11 is washed for the next measurement.

In other words, a high-pressure air is stored previously in the high-pressure air tank 39 by driving the compressor 40, and a given amount of washing water is transferred to the washing water storage tank 33 from the washing water supply tank 34 in advance. Before the storage of the high-pressure air and the transfer of the washing water, the switching valve 38 is switched to the second switching position where the washing water storage tank 33 does not communicate with the high-pressure air tank 39, but communicates with atmosphere.

Then, the water-immersed aggregate that has been measured is dropped into the mixer below by opening the bottom lid 11 in the above procedure. Thereafter, the switching valve 38 is switched to the first position.

With this operation, the high-pressure air stored in the high-pressure air tank 39 is forced into the washing water storage tank 33. The pressure causes the washing water in the measuring tank to spout from the washing nozzle 31 and to blow off the aggregate adhering on the top face of the bottom lid 11.

After the washing water is sprayed out once, the switching valve 38 is switched to the second position again to carry out the storage of the high-pressure air and the transfer of the washing water for the subsequent cleaning process after the measurement.

On the other hand, a percentage of surface moisture of each fine aggregate is calculated in addition to the aforementioned measurement of the fine aggregate A, the fine aggregate B, and the water. More specifically, the amount of supplied water $M_I$ to the measuring tank 5 is previously measured, and the percentages of surface moisture of the fine aggregate A and that of the fine aggregate B are calculated by using an accumulation value of the amount of absorbed water $M_O$ from the measuring tank 5 measured by the absorbed water measuring storage tank 17.

Concretely, the amount of supplied water $M_I$ to the measuring tank 5, the amount of absorbed water $M_O$ from the measuring tank 5, and the total mass $M_{fi}$ (i=1 to N) are substituted for the following formula to obtain $\Sigma M_{awj}$ (j=1 to i)

$$\Sigma M_{awj}(j=1 \text{ to } i) = M_{fi} - (M_I - M_O) \quad (5)$$

$M_{awi}$ is then calculated from the following formula:

$$M_{awi} = \Sigma M_{awj}(j=1 \text{ to } i) - \Sigma M_{awj}(j=1 \text{ to } (i-1)) \quad (6)$$

Thereafter, $M_{awi}$ is substituted for the following formula and a percentage of surface moisture is calculated:

$$(M_{awi} - M_{ai})/M_{ai} \quad (7)$$

Subsequently, with respect to the remaining one of the fine aggregate A and the fine aggregate B having been divided, a value measured as has been conventional in the aggregate measuring bin 51 is corrected by using the percentage of surface moisture calculated in this procedure.

As set forth hereinabove, according to the measuring apparatus 1 for concrete materials of this embodiment, the surface moisture of the fine aggregate A and that of the fine aggregate B are calculated indirectly as a part of the mass $M_w$ of the water in consideration of variation of aggregates whose moisture state is not uniform. In addition, the mass of each aggregate is calculated as the mass $M_{ai}$ (i=1 to N) of the aggregate in the saturated surface-dried condition. In other words, the mass of the aggregate and the water are calculated on the conditions equivalent to the specified mix proportion. Therefore, even if the humidity grade of the aggregate is not fixed at every measurement, it is possible to make concrete according to the specified mix proportion.

Furthermore, according to the measuring apparatus 1 for concrete materials of this embodiment, a water intake at a lower end of the suction pipe is previously positioned so that the water level of the water-immersed aggregate in the measuring tank 5 is held at a desired water level by moving the suction pipe 16 up and down appropriately by using the water level holding device 8. Therefore, water exceeding the desired water level as excess water is absorbed by the suction fan 18 via the suction pipe 16 after the water-immersed aggregate in the measuring tank 5 reaches the desired water level. As a result, a volume of the water-immersed aggregate in the measuring tank 5 can be held at a predetermined volume, thereby eliminating the need for measuring the volume.

More specifically, if the total mass $M_{fi}$ (i=1, 2) of the water-immersed aggregate reaches the target mass $M_{d2}$ of the water-immersed aggregate while excess water is absorbed to prevent the water-immersed aggregate from exceeding the first and second water levels, the total volume $V_{fi}$ (i=1, 2) of the water-immersed aggregate need not be measured, and further the total mass $M_{fi}$ (i=1, 2) of the water-immersed aggregate and the total volume $V_{fi}$ (i=1, 2) of the water-immersed aggregate are equal to the values set up first. Therefore, the field mix need not be corrected, and the water-immersed aggregate can be directly thrown into the kneading mixer together with other concrete materials and kneaded.

Still further, according to the measuring apparatus 1 for concrete materials of this embodiment, if the water of the water-immersed aggregate does not reach the preset first and second water levels at that time, water need be added so as to reach the first and second water levels. The total volume $V_{fi}$ (i=1, 2) of the water-immersed aggregate, however, need not be measured similarly to the above. Then, the total mass $M_{fi}$ (i=1, 2) of the water-immersed aggregate is measured again, by which the input of the fine aggregate A and that of the fine aggregate B are managed correctly and the field mix is corrected. As a result, it becomes possible to make concrete according to the specified mix proportion.

In addition, a plurality of aggregates different from one another in density, grading, or the like can be measured efficiently and very accurately within a single measuring tank, while accurately calculating the effects of the surface moisture caused by differences in the moisture state as a part of the final amount of water.

Furthermore, according to the measuring apparatus 1 for concrete materials of this embodiment, the electrode sensor 7 is disposed inside the hollow tube 21 and fixed to the suction pipe 16 with the hollow tube. The hollow tube 21 is arranged in a way that a low-pressure air flows through the hollow tube 21 in a vertical downward direction. Thereby, bubbles on the water surface in the measuring tank 5 can be removed by the low-pressure air flow, thus improving the accuracy in measurement of the electrode sensor 7. In addition, by previously positioning the electrode sensor 7 so that a lower end of the hollow tube 21 is slightly immersed in the water of the water-immersed aggregate at a position where a lower end of the electrode sensor 7 is in contact with the surface of the water-immersed aggregate, bubbles removed once are prevented from gathering again at the lower end of the electrode sensor 7.

According to the measuring apparatus 1 for concrete materials of-this embodiment, the bottom lid 11 is coupled to the measuring tank body 10 via the link members 41 and 42 different in the radius of gyration. Thereby, when the pressing force of the elevator rod 44 acts on the bottom lid 11, the bottom lid 11 rotates so as to turn to the side of the measuring tank body 10.

Therefore, it is possible to save a downward space in a height direction needed for opening the bottom lid 11 completely. In other words, in the conventional technology for the opening or closing operation, if the bottom lid is opened, it will hang down. Therefore, the opening-and-closing space for the bottom lid must be secured in the height direction conventionally. According to this embodiment, however, it is possible to reduce the downward opening-and-closing space. Therefore, the opening at the bottom of the measuring tank body 10 can be lowered correspondingly, and the aggregate can be reliably thrown into the kneading mixer.

Immediately before closing the bottom lid 11, the bottom lid 11 is put in a position substantially parallel to the bottom opening of the measuring tank body 10 due to the action of the above two link members 41 and 42. Therefore, a substantially uniform pressure is applied to a seal (not shown) provided at the bottom opening or the bottom lid 11. Thereby, uniform water tightness can be secured along the bottom opening, and a partial damage on the seal can be prevented.

Furthermore, according to the measuring apparatus 1 for concrete materials of this embodiment, washing water is sprayed on to the top face of the bottom lid 11 by using the washing water spraying device 30. Thereby, aggregate adhering on the top face of the bottom lid 11 at the time of discharge of the water-immersed aggregate will be washed away and blown off by the washing water. Therefore, when the bottom lid 11 is closed for the next measurement, aggregate is not caught between the measuring tank body 10 and the bottom lid 11.

Accordingly, it is possible to prevent an occurrence of an error in the measurement, which may be caused by a leakage of water from a clearance by aggregate caught between the measuring tank body and the bottom lid. Furthermore, it does not damage the seal members provided in the measuring tank body 10 and the bottom lid 11.

Still further, according to the measuring apparatus 1 for concrete materials of this embodiment, there are two types of means for measuring the fine aggregate A and the fine aggregate B supplied from the aggregate hopper 3: the measuring tank 5 for measuring water-immersed aggregate and the aggregate measuring bin 51 for measuring only the fine aggregate A and fine aggregate B. Therefore, even for concrete whose aggregate is large relative to water, for example, due to a poor mix with a low slump as compared with an ordinary quality of concrete, a certain amount of the fine aggregate A and that of the fine aggregate B are calculated accurately by means of the water-immersed aggregate measurement in the measuring tank 5. Regarding the remaining fine aggregates A and fine aggregate B, the measured values of the fine aggregate A and the fine aggregate B can be corrected with percentages of surface moisture with accuracy much higher than the conventional ones by using the percentages of surface moisture calculated in the process of the water-immersed aggregate measurement.

When taking into consideration the air content in the water-immersed aggregate (a %), still more accurate measurement can be performed with the actual total volume by replacing $V_{fi}$ (i=1, 2) with $V_{fi}$ (i=1, 2)·(1−a/100), though particular reference has not been made to this in the embodiment.

Furthermore, particular reference has not bee made to the following, too. If, however, the fine aggregate thrown into the measuring tank 5 is protruding from the water surface and it won't be water-immersed aggregate, the vibrator is lowered and operated during or after the supply of the fine aggregate A or B. Thereby, the fine aggregate A or B thrown into the measuring tank 5 will be flattened by vibration of the vibrator, thus preventing the fine aggregate from protruding from the water surface. Before measuring the mass of the water-immersed aggregate, the vibrator is lifted and put in a standby state in the upward location until the next measurement.

While this embodiment has been described by giving an example of two kinds of fine aggregate, naturally the number of kinds of aggregate is arbitrary. The present invention is naturally applicable to a single kind of fine aggregate, to only coarse aggregate, and to a combination of fine aggregate and coarse aggregate.

Furthermore, while the load cell 6 is of the compression type and is placed in three places, an arbitrary type of load cell can be used as means for measuring mass of water-immersed aggregate. For example, an extension-type load cell can be used, and it is possible to place the load cell in four or more places. If the measuring tank 5 can be held in a stable and suspended condition, the load cell can be placed in one or two places.

Furthermore, while the washing water supply means comprises the washing water supply valve 37, the flow regulating valve 36, the washing water pump 35, and the washing water supply tank 34, the washing water supply means of the present invention can be arbitrarily configured.

Instead of the above configuration, the washing water supply means can comprise, for example, a water pipe and a valve provided at the water pipe.

[Second Embodiment]

A measuring apparatus for concrete materials according to a second embodiment will now be described below. The same reference numerals have been retained for substantially the same parts as for the first embodiment, and their description is omitted here.

Referring to FIG. 4, there is shown a general view of the measuring apparatus according to this embodiment. As shown in FIG. 4, the measuring apparatus 61 for concrete materials according to this embodiment generally comprises: an aggregate hopper 3 as aggregate feed means for feeding fine aggregate 2 as aggregate; a water supply pipe 4 as water supply means; a measuring tank 5 for storing the fine aggregate 2 supplied from the aggregate hopper 3 as water-immersed aggregate together with water supplied through the water supply pipe 4; a load cell 6 as water-immersed aggregate mass measuring means for measuring mass of the water-immersed aggregate in the measuring tank; an electrode sensor 7 as water level measuring means for measuring the water level of the water-immersed aggregate in the measuring tank; and a water level holding device 8 as water level holding means for holding the water level of the water-immersed aggregate in the measuring tank 5 at a desired water level.

Since the aggregate hopper 3, the load cell 6, the water supply pipe 4, and the measuring tank 5 have already been described in the first embodiment, their detailed description is omitted here. Similarly to the first embodiment, an elevating gate 12 working with the load cell 6 is provided in the opening at the lower end of the aggregate hopper 3. By closing the elevating gate 12 according to the mass value measured by the load cell 6, the supply of the fine aggregate 2 to the measuring tank 5 can be stopped.

Furthermore, under the opening at the lower end of the aggregate hopper 3, there is provided a vibrating feeder 13 having an electromagnetic vibrator extending to the upper opening of the measuring tank 5. The fine aggregate 2 is conveyed from under the aggregate hopper 3 to the upper opening of the measuring tank 5 by using the vibrating feeder, thereby preventing granulation of the fine aggregate and therefore preventing mixing of air bubbles.

The electrode sensor 7 is connected to a self-powered sensor controller 15, similarly to the first embodiment. It can measure the water level of water-immersed aggregate by monitoring changes in an energized condition when its lower end is put in contact with the water surface of the water-immersed aggregate in the measuring tank 5. In this event, one electrode terminal of a power supply, which is not shown, incorporated in the sensor controller 15 is electrically connected to the electrode sensor 7, and the other electrode terminal is electrically connected to the measuring tank 5 made of, for example, steel.

Similarly to the first embodiment, the water level holding device 8 comprises a suction pipe 16 placed so as to move up and down freely, an absorbed water measuring storage tank 17, which is connected so as to communicate with the suction pipe, for measuring absorbed water, and a suction fan 18 as suction means connected so as to communicate with the absorbed water measuring storage tank. Thereby, the absorbed water measuring storage tank 17 can measure the mass of water absorbed by load cell 19.

The suction pipe 16 is coupled to a piston rod of a suction pipe elevation actuator 20 attached to the side face of the measuring body 10. Thereby, the suction pipe can be moved up and down freely by driving the suction pipe elevation actuator. For the suction pipe elevation actuator 20, it is preferable to use, for example, an electric servo cylinder, to secure the precision in elevation.

The above electrode sensor 7 is disposed inside a hollow tube 21 and the hollow tube is fixed to the suction pipe 16, similarly to the first embodiment described with reference to FIG. 2(a). More specifically, the hollow tube 21 and the electrode sensor 7 disposed inside it are arranged so as to move up and down by using the suction pipe elevation actuator 20, working with the suction pipe 16.

On the other hand, the hollow tube 21 is connected at its upper end to a low-pressure air pump 22 as low-pressure air intake means, for example, via a vinyl tube. Thereby, a low-pressure air flows through the hollow tube 21 in a vertical downward direction by driving the low-pressure air pump 22.

The bottom lid 11 is coupled to the side face of the measuring tank body 10 via a shorter link member 41 and a link member 42 longer than the link member 41, similarly to the first embodiment described with reference to FIG. 3. Thereby, when the bottom lid is pressed down, it can rotate turning to the side of the measuring tank body 10 due to a smaller radius of gyration of the link member 41 and a larger radius of gyration of the link member 42.

Furthermore, bottom lid control actuators 43, 43 are placed so that they can be fixed to the side face of the measuring tank body 10 at the lower end. A tip of a piston rod of the bottom lid control actuator is coupled to a tip of an elevator rod 44 pinned to the bottom lid 11 via a coupling member 45. The coupling member 45 is mated with a vertical guide 46 so that it can slide freely along the vertical guide 46 provided in an extended condition on the side face of the measuring tank body 10.

On the other hand, the measuring apparatus 61 for concrete materials according to this embodiment is provided with a washing water spraying device 30 as washing water spraying means for spraying washing water on the top face of the bottom lid 11. Since it has already been described in the first embodiment, the description is omitted here.

For a description of a procedure for measuring the fine aggregate 2 by using the measuring apparatus 61 for concrete materials according to this embodiment, it is assumed that the fine aggregate 2 comprises two kinds of fine aggregate A and B and that they are sequentially supplied. A procedure for measuring the water and the fine aggregate 2 is almost the same as the first embodiment. Therefore, its detailed description is omitted appropriately here.

First, a water intake at a lower end of the suction pipe 16 is previously positioned so that the water level of the water-immersed aggregate in the measuring tank 5 is held at a desired water level by driving the suction pipe elevation actuator 20 to move the suction pipe 16 up and down appropriately. Whether the water level in the measuring tank 5 remains at the desired water level is checked separately by using the electrode sensor 7 as water level measuring means.

Subsequently, target mass $M_{di}$ (i=1, 2) is set for water-immersed aggregate at an end of supplying the fine aggregate A and the fine aggregate B. A method of setting the target mass $M_{di}$ (i=1, 2) is as set forth in the first embodiment.

Then, the fine aggregate A and water are thrown into the measuring tank 5 in the same manner as for the first embodiment. Before throwing the water and the fine aggregate A into the measuring tank 5, the suction pipe 6 of the water-level holding device 8 is appropriately moved up and down to position the water intake, which is provided at the lower end of the suction pipe 16, so that the water level of the water-immersed aggregate in the measuring tank 5 is held at the first water level, which is the desired water level.

Subsequently, total mass $M_{f1}$ of the water-immersed aggregate is measured with the load cell 6. The total mass $M_{f1}$ of the water-immersed aggregate can be measured by subtracting the mass of only the measuring tank 5 from the mass of the measuring tank 5 filled with the water-immersed aggregate.

Regarding a procedure for measuring the total mass $M_{f1}$ of the water-immersed aggregate, similarly to the first embodiment, the total mass $M_{f1}$ of the water-immersed aggregate is measured in real time or at predetermined time intervals while the fine aggregate A is supplied continuously or intermittently at a predetermined rate. If the total mass $M_{f1}$ of the water-immersed aggregate reaches the target mass $M_{d1}$ of the water-immersed aggregate while excess water is absorbed by using the water level holding device 8 to prevent the water level of the water-immersed aggregate from exceeding the preset first water level as a desired water level, the supply of the fine aggregate A is ended.

Since the elevating gate 12 provided in the opening at the lower end of the aggregate hopper 3 is linked with the load cell 6, the elevating gate 12 is closed in response to a control signal from the load cell 6 when the total mass $M_{f1}$ of the water-immersed aggregate has reached the target mass $M_{d1}$ of the water-immersed aggregate, by which the supply of the fine aggregate A is automatically stopped.

Furthermore, it is checked that the water level at the end of the supply has reached the first water level separately by using the electrode sensor 7. When the water level increases due to the supply of the fine aggregate A and is coming close to the first water level, the low-pressure air pump 22 is operated to feed a low-pressure air into the hollow tube 21. Thereby, as shown in FIG. 2(b), bubbles on the water surface of the water-immersed aggregate are blown away to the outside of the hollow tube 21. Therefore, when the water level of the water-immersed aggregate in the measuring tank 5 has reached the first water level, the water level can be precisely detected with the electrode sensor 7, not being disturbed by bubbles on the surface of the water-immersed aggregate, as shown in FIG. 2(c).

Subsequently, mass $M_{a1}$ of the fine aggregate A in the saturated surface-dried condition is calculated from formula (1), where $\rho_{a1}$ is a density of the fine aggregate A in the saturated surface-dried condition, $\rho_w$ is a density of the water, $M_{f1}$ is a total mass of the water-immersed aggregate, and $V_{f1}$ is a total volume of the water-immersed aggregate obtained for the preset first water level.

On the other hand, when the total mass $M_{f1}$ of the water-immersed aggregate has reached the target mass $M_{d1}$ of the water-immersed aggregate and if it is confirmed with the electrode sensor 7 that the water of the water-immersed aggregate does not reach the preset first water level, water is added so as to reach the first water level. Thereafter, the total mass $M_{f1}$ of the water-immersed aggregate is measured again and recalculation is made for the mass $M_{a1}$ of the fine aggregate A in the saturated surface-dried condition.

Thereafter, the fine aggregate B is thrown into the measuring tank 5 so as to obtain water-immersed aggregate in which the fine aggregate does not protrude from the water surface similarly to the fine aggregate A.

In other words, similarly the suction pipe 16 is appropriately moved up and down previously to position the water intake provided at the lower end of the suction pipe 16 so that the water level of the water-immersed aggregate in the measuring tank 5 is held at the second water level as a desired water level.

The total mass $M_{f2}$ of the water-immersed aggregate is measured, next. In measuring the total mass $M_{f2}$ of the water-immersed aggregate, similarly to the fine aggregate A, the fine aggregate B is supplied continuously or intermittently at a predetermined rate, while the total mass $M_{f2}$ of the water-immersed aggregate is measured in real time or at predetermined time intervals. During the supply of the fine aggregate B, excess water is absorbed by using the water level holding device 8 to prevent the water level of the water-immersed aggregate from exceeding the preset second water level as a desired water level. When the total mass $M_{f2}$ of the water-immersed aggregate has reached the target mass $M_{d2}$ of the water-immersed aggregate, the supply of the fine aggregate B is ended.

Similarly to the fine aggregate A, it is checked that the water level at the end of the supply has reached the second water level separately by using the electrode sensor 7. When the water level increases due to the supply of the fine aggregate B and is coming close to the second water level, the low-pressure air pump 22 is operated to feed an low-pressure air into the hollow tube 21. Thereby, the water level can be precisely detected with the electrode sensor 7, not being disturbed by bubbles on the surface of the water-immersed aggregate as mentioned above.

Subsequently, mass $M_{a2}$ of the fine aggregate B in the saturated surface-dried condition and mass of water $M_w$ are calculated from formulas (3) and (4), where $\rho_{a1}$ is a density of the fine aggregate A in the saturated surface-dried condition, $\rho_{a2}$ is a density of the fine aggregate B in the saturated surface-dried condition, $\rho_w$ is a density of the water, $M_{f2}$ is a total mass of the water-immersed aggregate, and $V_{f2}$ is a total volume of the water-immersed aggregate obtained for the preset second water level.

On the other hand, when the total mass $M_{f2}$ of the water-immersed aggregate has reached the target mass $M_{d2}$ thereof and if it is confirmed with the electrode sensor 7 that the water of the water-immersed aggregate does not reach the preset second water level, water is added so that it reaches the second water level. Thereafter, the total mass $M_{f2}$ of the water-immersed aggregate is measured again and recalculation is made for the mass $M_{a2}$ of the fine aggregate B in the saturated surface-dried condition and for the mass $M_w$ of the water.

After measuring the fine aggregate A, the fine aggregate B, and the water in this manner, the result of the measurement is compared with the initial field mix set according to the specified mix proportion, and the field mix is corrected, if necessary.

More specifically, if the total mass $M_{fi}$ (i=1, 2) of the water-immersed aggregate reaches the target mass $M_{d2}$ of the water-immersed aggregate while excess water is absorbed to prevent the water-immersed aggregate from exceeding the first and second water levels, the total mass $M_{fi}$ (i=1, 2) of the water-immersed aggregate and the total volume $V_{fi}$ (i=1, 2) of the water-immersed aggregate are equal to the values set up first. In this case, the field mix need not be corrected. Therefore, the water-immersed aggregate is directly thrown into the kneading mixer together with other concrete materials and kneaded.

On the other hand, the level of the water-immersed aggregate does not reach the preset first and second water levels, water is added so that it reaches the first and second water levels. As a result, the total mass $M_{fi}$ (i=1, 2) of the re-measured water-immersed aggregate, and thus the mass of the fine aggregate A and that of the fine aggregate B in the saturated surface-dried condition calculated from the total mass $M_{fi}$ (i=1, 2) are different from the values set up first.

Therefore, in this case, the mass of the measured fine aggregate A and that of the fine aggregate B are compared with the mass of the fine aggregate A and that of the fine aggregate B of the field mix set up first to calculate a ratio of a mass summation of the measured fine aggregate A and fine aggregate B in the saturated surface-dried condition to a mass summation of the preset fine aggregate A and fine aggregate B in the saturated surface-dried condition. For example, if it is 0.9, the mass of the measured fine aggregate A and fine aggregate B is 10% less than the preset value. Therefore, the mixing volume of one batch No itself need be decreased by 10% to get $0.9 \cdot N_0$. Accordingly, the ratio is also applied to other concrete materials such as cement and a chemical admixture to correct the initial field mix and re-measure according to the corrected field mix. For the water, similarly the preset amount of water is compared with the measured amount of water. Water is then added to supply the deficiency of water as secondary water, or excess water is drained. Thereafter, these concrete materials are thrown into the kneading mixer and kneaded.

To open the bottom lid 11 to take out the water-immersed aggregate that has been measured, drive the bottom lid control actuators 43, 43 to retract the piston rod, as described in the first embodiment with reference to FIG. 3.

After throwing the measured water-immersed aggregate into the mixer, the bottom lid 11 is washed for the next measurement.

In other words, a high-pressure air is stored previously in the high-pressure air tank 39 by driving the compressor 40, and a given amount of washing water is transferred to the washing water storage tank 33 from the washing water supply tank 34 in advance. Before the storage of the high-pressure air and the transfer of the washing water, the switching valve 38 is switched to the second switching position where the washing water storage tank 33 does not communicate with the high-pressure air tank 39, but communicates with atmosphere.

Then, the measured water-immersed aggregate is dropped into the mixer below by opening the bottom lid 11 in the above procedure. Thereafter, the switching valve 38 is switched to the first position.

With this operation, the high-pressure air stored in the high-pressure air tank 39 is forced into the washing water storage tank 33. The pressure causes the washing water in the measuring tank to spout from the washing nozzle 31 and to blow off the aggregate adhering on the top face of the bottom lid 11.

After the washing water is sprayed out once, the switching valve 38 is switched to the second position again to carry out the storage of the high-pressure air and the transfer of the washing water for the subsequent cleaning process after measurement.

As set forth hereinabove, according to the measuring apparatus 61 for concrete materials of this embodiment, the surface moisture of the fine aggregate A and that of the fine aggregate B are calculated indirectly as a part of the mass $M_w$ of the water in consideration of variation of aggregates whose moisture state is not uniform. In addition, the mass of each aggregate is calculated as the mass $M_{ai}$ (i=1 to N) of the aggregate in the saturated surface-dried condition. In other words, the mass of the aggregate and the mass of the water are calculated on the conditions equivalent to the specified mix proportion. Therefore, even if the humidity grade of the aggregate is not fixed at every measurement, it is possible to make concrete according to the specified mix proportion.

Furthermore, according to the measuring apparatus 61 for concrete materials of this embodiment, a water intake at a lower end of the suction pipe is previously positioned so that the water level of the water-immersed aggregate in the measuring tank 5 is held at a desired water level by moving the suction pipe 16 up and down appropriately by using the water level holding device 8. Therefore, water exceeding the desired water level as excess water is absorbed by the suction fan 18 via the suction pipe 16 after the water-immersed aggregate in the measuring tank 5 reaches the desired water level. As a result, a volume of the water-immersed aggregate in the measuring tank 5 can be held at a predetermined volume, thereby eliminating the need for measuring the volume.

More specifically, if the total mass $M_{fi}$ (i=1, 2) of the water-immersed aggregate reaches the target mass $M_{d2}$ of the water-immersed aggregate while excess water is drained by using the water level holding device 8 to prevent the water-immersed aggregate from exceeding the first and second water levels, the total mass $M_{fi}$ (i=1, 2) of the water-immersed aggregate and the total volume $V_{fi}$ (i=1, 2) of the water-immersed aggregate are equal to the values set up first. Therefore, the field mix need not be corrected, and the water-immersed aggregate can be directly thrown into the kneading mixer together with other concrete materials and kneaded.

Still further, according to the measuring apparatus 61 for concrete materials of this embodiment, if the water of the water-immersed aggregate does not reach the preset first and second water levels at that time, water need be added so as to reach the first and second water levels. The total volume $V_{fi}$ (i=1, 2) of the water-immersed aggregate, however, need not be measured similarly to the above. Then, the total mass $M_{fi}$ (i=1, 2) of the water-immersed aggregate is measured again, by which the input of the fine aggregate A and that of the fine aggregate B are managed correctly and the field mix is corrected. As a result, it becomes possible to make concrete according to the specified mix proportion.

In addition, a plurality of aggregates different from one another in density, grading, and the like can be measured efficiently and very accurately within a single measuring tank, while accurately calculating the effects of the surface moisture caused by differences in the moisture state as a part of the final amount of water.

Furthermore, according to the measuring apparatus 61 for concrete materials of this embodiment, the electrode sensor 7 is disposed inside the hollow tube 21 and fixed to the suction pipe 16 with the hollow tube. The hollow tube 21 is arranged in a way that a low-pressure air flows through the hollow tube 21 in a vertical downward direction. Thereby, bubbles on the water surface in the measuring tank 5 can be removed by the low-pressure air flow, thus improving the accuracy in measurement of the electrode sensor 7. In addition, by previously positioning the electrode sensor 7 so that a lower end of the hollow tube 21 is slightly immersed in the water of the water-immersed aggregate at a position where a lower end of the electrode sensor 7 is in contact with the surface of the water-immersed aggregate, bubbles removed once are prevented from gathering again at the lower end of the electrode sensor 7.

According to the measuring apparatus 61 for concrete materials of this embodiment, the bottom lid 11 is coupled to the measuring tank body 10 via the link members 41 and 42 different in the radius of gyration. Thereby, when the pressing force of the elevator rod 44 acts on the bottom lid 11, the bottom lid 11 rotates so as to turn to the side of the measuring tank body 10.

Therefore, it is possible to save a downward space in a height direction needed for opening the bottom lid 11 completely. In other words, in the conventional technology for the opening or closing operation, if the bottom lid is opened, it will hang down. Therefore, the opening-and-closing space for the bottom lid must be secured in the height direction conventionally. According to this embodiment, however, it is possible to reduce the downward opening-and-closing space. Therefore, the opening at the bottom of the measuring tank body 10 can be lowered correspondingly, and the aggregate can be reliably thrown into the kneading mixer.

Immediately before closing the bottom lid 11, the bottom lid 11 is put in a position substantially parallel to the bottom opening of the measuring tank body 10 due to the action of the above two link members 41 and 42. Therefore, a substantially uniform pressure is applied to a seal (not shown) provided at the bottom opening or the bottom lid 11. Thereby, uniform water tightness can be secured along the bottom opening, and a partial damage on the seal can be prevented.

Furthermore, according to the measuring apparatus 61 for concrete materials of this embodiment, washing water is sprayed on to the top face of the bottom lid 11 by using the washing water spraying device 30. Thereby, aggregate adhering on the top face of the bottom lid 11 at the time of discharge of the water-immersed aggregate will be washed away and blown off by the washing water. Therefore, when the bottom lid 11 is closed for the next measurement, aggregate is not caught between the measuring tank body 10 and the bottom lid 11.

Accordingly, it is possible to prevent an occurrence of an error in the measurement, which may be caused by a leakage of water from a clearance by aggregate caught between the measuring tank body and the bottom lid. Furthermore, it does not damage the seal members provided in the measuring tank body 10 and the bottom lid 11.

While particular reference has not been made to the following, if the amount of supplied water $M_I$ to the measuring tank is previously measured by, for example, the load cell 6, the accumulation value of the water absorbed from the measuring tank 5 can be measured by the load cell 19 of the absorbed water measuring storage tank 17. Therefore, the percentage of surface moisture of the aggregate can be accurately measured.

In other words, substitute the amount of supplied water $M_I$ to the measuring tank 5, the amount of absorbed water $M_o$ from the measuring tank 5 measured by the load cell 19, and the total mass $M_{fi}$ (i=1, 2) for the formula (5) to obtain $\Sigma M_{awj}$ (j=1 to i) Then substitute $M_{awi}$ calculated from the formula (6) for the formula (7). Thereby, percentages of surface moisture of the fine aggregate A and the fine aggregate B can be calculated and they can be used as setting values for the next measurement.

When taking into consideration the air content in the water-immersed aggregate (a %), still more accurate measurement can be performed with the actual total volume by replacing $V_{fi}$ (i=1, 2) with $V_{fi}$ (i=1, 2)·(1−a/100), though particular reference has not been made to it in this embodiment.

Particular reference has not bee made to the following, too. If, however, the fine aggregate thrown into the measuring tank 5 is protruding from the water surface and it won't be water-immersed aggregate, the vibrator is lowered and operated during or after the supply of the fine aggregate A or B. Thereby, the fine aggregate A or B thrown into the measuring tank 5 will be flattened by vibration of the vibrator, thus preventing the fine aggregate from protruding from the water surface. Before measuring the mass of the water-immersed aggregate, the vibrator is lifted and put in a standby state in the upward location until the next measurement.

While this embodiment has been described by giving an example of two kinds of fine aggregate, naturally the number of kinds of aggregate is arbitrary. The present invention is naturally applicable to a single kind of fine aggregate, to only coarse aggregate, and to a combination of fine aggregate and coarse aggregate.

Furthermore, while the load cell 6 is of the compression type and is placed in three places, an arbitrary type of load cell can be used as means for measuring mass of water-immersed aggregate. For example, an extension-type load cell can be used, and it is possible to place a load cell in four or more places. If the measuring tank 5 can be held in a stable and suspended condition, the load cell can be placed in one or two places.

Furthermore, while the washing water supply means comprises the washing water supply valve 37, the flow regulating valve 36, the washing water pump 35, and the washing water supply tank 34, the washing water supply means of the present invention can be arbitrarily configured. Instead of the above configuration, the washing water supply means can comprise, for example, a water pipe and a valve provided at the water pipe.

INDUSTRIAL APPLICABILITY

According to the measuring apparatus for concrete materials of the present invention, even for concrete whose aggregate is large relative to water, for example, due to a poor mix with a low slump as compared with an ordinary quality of concrete, a certain amount of fine aggregate is calculated accurately by means of the water-immersed aggregate measurement in the measuring tank 5. Regarding the remaining fine aggregate, the measured values of the fine aggregate can be corrected with a percentage of surface moisture with accuracy much higher than the conventional one by using the percentage of surface moisture calculated in the process of the water-immersed aggregate measurement.

Furthermore, according to the measuring apparatus for concrete materials of the present invention, the surface moisture of the aggregate can be calculated indirectly as a part of the mass $M_w$ of the water in consideration of variation of aggregates whose moisture state is not uniform. In addition, the mass of each aggregate can be calculated as the mass $M_a$ of the aggregate in the saturated surface-dried condition. In other words, the mass of the aggregate and the water are calculated on the conditions equivalent to the specified mix proportion. Therefore, even if the humidity grade of the aggregate is not fixed at every measurement, it is possible to make concrete by the amount of water as specified in the specified mix proportion, without a need for measuring the percentage of surface moisture.

Furthermore, for concrete materials, both fine aggregate and coarse aggregate are needed and further it is expected to use a plurality of kinds of fine or coarse aggregates different from one another in density or grading. Particularly, it is often important to make new aggregate having desired grading for concrete mixing by mixing a plurality of aggregates different from one another in grading at an appropriate proportion. The measuring apparatus for concrete materials of the present invention is very useful for measuring the plurality of aggregates different from one another in at least one of density and grading.

What is claimed is:

1. A measuring apparatus for concrete materials, comprising:
   aggregate feed means for feeding aggregate;
   water supply means;
   an aggregate measuring bin for storing and measuring aggregate supplied from said aggregate feed means;
   a measuring tank for storing aggregate supplied from said aggregate feed means as water-immersed aggregate together with water supplied from said water supply means, with a bottom lid capable of maintaining water tightness attached at a bottom opening in such a way as to be free to open or close;
   water-immersed aggregate mass measuring means for measuring mass of water-immersed aggregate in said measuring tank;
   water level measuring means for measuring a water level of the water-immersed aggregate in said measuring tank; and
   water level holding means for absorbing water exceeding a desired water level from said measuring tank to hold the desired water level of the water-immersed aggregate in said measuring tank and for measuring an amount of the absorbed water,
   wherein the water level holding means comprises a suction pipe placed so as to move up and down freely, an absorbed water measuring storage tank, which is connected so as to communicate with the suction pipe, for measuring the absorbed water, and suction means connected so as to communicate with the absorbed water measuring storage tank; and
   wherein said aggregate feed means can feed the aggregate to said aggregate measuring bin and said measuring tank.

2. The measuring apparatus for concrete materials according to claim 1, wherein said water level measuring means comprise an electrode sensor and wherein the electrode sensor is fixed to said suction pipe so that said electrode sensor can move up and down in conjunction with said suction pipe.

3. The measuring apparatus for concrete materials according to claim 2, wherein said electrode sensor is disposed inside a hollow tube and fixed to said suction pipe together with the hollow tube and wherein low-pressure air intake means is provided at an upper end of the hollow tube so that a low-pressure air flows in a vertical downward direction into said hollow tube.

4. The measuring apparatus for concrete materials according to claim 1, further comprising washing water spraying means capable of spraying washing water on a top face of said bottom lid from a washing nozzle attached in the vicinity of said bottom lid, wherein the washing water spraying means comprises a washing water storage tank connected to said washing nozzle, washing water supply means connected to the washing water storage tank, a high-pressure air tank connected so as to communicate with said washing water storage tank via a switching valve, and a compressor connected to the high-pressure air tank and wherein said switching valve is arranged in such a way that said washing water storage tank communicates with said high-pressure air tank in a first switching position and that said washing water storage tank communicates with atmosphere in a second switching position.

5. The measuring apparatus for concrete materials according to claim 1, wherein said bottom lid is coupled to a body of said measuring tank via link members having different lengths so that the bottom lid rotates while moving toward the side of said measuring tank body, wherein a predetermined bottom lid control actuator is installed in such a way as to be fixed at its lower end on the side face of said measuring tank body, wherein a tip of a piston rod of the bottom lid control actuator is coupled to a tip of an elevator rod pinned at the bottom lid via a predetermined coupling member, and wherein the coupling member is mated with a vertical guide member provided in an extended condition on the side face of the measuring tank body so that the coupling member can slide freely along said vertical guide member.

6. A measuring apparatus for concrete materials, comprising:
   aggregate feed means for feeding aggregate;
   water supply means;
   a measuring tank for storing aggregate supplied from said aggregate feed means as water-immersed aggregate together with water supplied from said water supply means, having a bottom lid capable of maintaining water tightness attached at a bottom opening in such a way as to be free to open or close;
   water-immersed aggregate mass measuring means for measuring mass of water-immersed aggregate in said measuring tank;
   water level measuring means for measuring a water level of the water-immersed aggregate in said measuring tank; and
   water level holding means for absorbing water exceeding a desired water level from said measuring tank to hold the desired water level of the water-immersed aggregate in said measuring tank and for measuring an amount of the absorbed water,
   wherein the water level holding means comprises a suction pipe placed so as to move up and down freely, an absorbed water measuring storage tank, which is connected so as to communicate with the suction pipe, for measuring the absorbed water, and suction means connected so as to communicate with the absorbed water measuring storage tank.

7. The measuring apparatus for concrete materials according to claim 6, wherein said water level measuring means comprise an electrode sensor and wherein the electrode sensor is fixed to said suction pipe so that said electrode sensor can move up and down in conjunction with said suction pipe.

8. The measuring apparatus for concrete materials according to claim 6, further comprising washing water spraying means capable of spraying washing water on a top face of said bottom lid from a washing nozzle attached in the vicinity of said bottom lid, wherein the washing water spraying means comprises a washing water storage tank connected to said washing nozzle, washing water supply means connected to the washing water storage tank, a high-pressure air tank connected so as to communicate with said washing water storage tank via a switching valve, and a compressor connected to the high-pressure air tank and wherein said switching valve is arranged in such a way that said washing water storage tank communicates with said high-pressure air tank in a first switching position and that said washing water storage tank communicates with atmosphere in a second switching position.

9. The measuring apparatus for concrete materials according to claim 6, wherein said bottom lid is coupled to a body of said measuring tank via link members having different lengths so that the bottom lid rotates while moving toward the side of said measuring tank body, wherein a predetermined bottom lid control actuator is installed in such a way as to be fixed at its lower end on the side face of said measuring tank body, wherein a tip of a piston rod of the bottom lid control actuator is coupled to a tip of an elevator rod pinned at the bottom lid via a predetermined coupling member, and wherein the coupling member is mated with a vertical guide member provided in an extended condition on the side face of the measuring tank body so that the coupling member can slide freely along said vertical guide member.

* * * * *